(12) United States Patent
Delmas et al.

(10) Patent No.: US 11,514,624 B2
(45) Date of Patent: Nov. 29, 2022

(54) METHODS AND SYSTEMS FOR BIOPSY NEEDLE RECONSTRUCTION ERROR ASSESSMENT

(71) Applicant: GE Precision Healthcare LLC, Milwaukee, WI (US)

(72) Inventors: Charlotte Delmas, Paris (FR); Jorge Corsino Espino, Paris (FR); Razvan Iordache, Paris (FR); Serge Calisti, Marseilles (FR); Laurence Vancamberg, Poissy (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 360 days.

(21) Appl. No.: 16/820,049

(22) Filed: Mar. 16, 2020

(65) Prior Publication Data
US 2021/0287409 A1   Sep. 16, 2021

(51) Int. Cl.
| | |
|---|---|
| A61B 6/00 | (2006.01) |
| G06T 11/00 | (2006.01) |
| A61B 6/02 | (2006.01) |
| A61B 6/04 | (2006.01) |
| A61B 6/12 | (2006.01) |
| A61B 10/02 | (2006.01) |
| G06T 7/00 | (2017.01) |

(52) U.S. Cl.
CPC ........... *G06T 11/008* (2013.01); *A61B 6/025* (2013.01); *A61B 6/0414* (2013.01); *A61B 6/12* (2013.01); *A61B 6/461* (2013.01); *A61B 6/502* (2013.01); *A61B 6/582* (2013.01); *A61B 10/0275* (2013.01); *G06T 7/0012* (2013.01); *G06T 2207/10112* (2013.01); *G06T 2207/10116* (2013.01); *G06T 2207/30068* (2013.01)

(58) Field of Classification Search
CPC .................. A61B 6/025; A61B 6/0414; G06T 2207/10112
See application file for complete search history.

(56) References Cited

U.S. PATENT DOCUMENTS

2018/0165840 A1* 6/2018 Bernard ................. A61B 34/10

OTHER PUBLICATIONS

Abdsaleh, S., "Core Biopsy of Breast and Axillary Lesions: Technical and Clinical Aspects," Doctor of Philosophy Dissertation, Faculty of Medicine, Uppsala University, Mar. 31, 2006, 42 pages.
Zhan,Y. et al., "Targeted Prostate Biopsy Using Statistical Image Analysis," IEEE Transactions on Medical Imaging, vol. 26, No. 6, Jun. 2007, 10 pages.

* cited by examiner

*Primary Examiner* — Dani Fox

(57) ABSTRACT

Methods and systems are provided for reconstruction error assessment for an interventional tool utilized in an image guided interventional procedure. In one example, an error model based on a target lesion position within a tissue, one or more interventional tool parameters, and imaging system parameters may be utilized to estimate an expected reconstruction error for the interventional tool. In another example, when the interventional tool is within the tissue, the expected reconstruction error may be utilized along with observed tool shape and size to infer an actual tool position and shape within the tissue.

20 Claims, 14 Drawing Sheets

Reconstruction error table for a needle tip location 54 mm above the detector

|  |  | Needle Diameter D (mm) | | | | |
| --- | --- | --- | --- | --- | --- | --- |
|  |  | 1 | 2 | 3 | 4 | 5 |
| Needle length L (mm) | 1 | 1.1 | 3.3 | 5.5 | 7.6 | 9.8 |
|  | 2 | 0.1 | 2.3 | 4.4 | 6.6 | 8.8 |
|  | 3 | 0 | 1.3 | 3.4 | 5.6 | 7.8 |
|  | 4 | 0 | 0.3 | 2.4 | 4.6 | 6.8 |
|  | 5 | 0 | 0 | 1.4 | 3.6 | 5.8 |
|  | 6 | 0 | 0 | 0.4 | 2.6 | 4.7 |
|  | 7 | 0 | 0 | 0 | 1.6 | 3.7 |
|  | 8 | 0 | 0 | 0 | 0.6 | 2.7 |
|  | 9 | 0 | 0 | 0 | 0 | 1.7 |
|  | 10 | 0 | 0 | 0 | 0 | 0.7 |

Reconstruction error table for a target needle tip location 20 mm above the detector

|  |  | Needle Diameter D (mm) | | | | |
| --- | --- | --- | --- | --- | --- | --- |
|  |  | 1 | 2 | 3 | 4 | 5 |
| Needle length L (mm) | 1 | 1.3 | 3.5 | 5.8 | 8.1 | 10.5 |
|  | 2 | 0.3 | 2.5 | 4.8 | 7.1 | 9.4 |
|  | 3 | 0 | 1.5 | 3.8 | 6.1 | 8.4 |
|  | 4 | 0 | 0.5 | 2.8 | 5.1 | 7.4 |
|  | 5 | 0 | 0 | 1.8 | 4.1 | 6.4 |
|  | 6 | 0 | 0 | 0.8 | 3.1 | 5.4 |
|  | 7 | 0 | 0 | 0.2 | 2.1 | 4.4 |
|  | 8 | 0 | 0 | 0 | 1 | 3.3 |
|  | 9 | 0 | 0 | 0 | 0 | 2.3 |
|  | 10 | 0 | 0 | 0 | 0 | 1.3 |

FIG. 4

Target position ($X_{target}, Y_{target}, Z_{target}$)

US 11,514,624 B2

METHODS AND SYSTEMS FOR BIOPSY NEEDLE RECONSTRUCTION ERROR ASSESSMENT

FIELD

Embodiments of the subject matter disclosed herein relate to mammography and mammography driven interventional procedures such as biopsy procedures, and more particularly, to evaluating image reconstruction error during Digital Breast Tomosynthesis (DBT) guided breast interventional procedures using needle like shaped interventional tools, such as needles used in biopsy procedures.

BACKGROUND

Mammography is a medical imaging procedure for detecting one or more tumors of a breast. Based on mammography imaging, an interventional procedure may be performed to reach the tumor area and either obtain a biopsy sample of the concerned breast tissue for further analysis, or put in place a hook for later surgery operation, or a local cryoablation. During a mammography procedure, the breast is compressed with a compression paddle, and positioned for interventional procedure. Location of a target tissue (e.g., lesion, microcalcification, etc.) is then identified based on a mammography imaging procedure, such as Digital Breast Tomosynthesis (DBT). For example, during DBT, a scout image (where x-ray tube is in a midline position perpendicular to the detector) and a plurality of projection images (where the x-ray tube moves in an arc at various angles within a set degree from the midline in both the positive and negative directions) are obtained. The projection images are reconstructed to obtain a DBT volume rendering of the breast. A target location within a region of interest (ROI) may be then selected based on the acquired DBT volume. In biopsy procedure, upon selecting the target, a biopsy tool is inserted into the breast, and a portion of the target tissue is excised with the biopsy tool to obtain the biopsy sample. In order to improve biopsy precision, assessment of biopsy tool position is desired. Tool position assessment may be desired for other interventional procedures (other than breast biopsy) such as, but not limited to, cryoablation, hook placement etc., which require positioning an interventional tool.

BRIEF DESCRIPTION

In one embodiment, a method for an x-ray system, comprises: performing a digital breast tomosynthesis scan on a compressed breast with the x-ray system and generating tomosynthesis scan data; reconstructing images of the compressed breast from the tomosynthesis scan data; and determining an expected reconstruction error for an interventional tool based on an error model modelled as a function of acquisition geometry of the x-ray system and interventional tool parameters; wherein the interventional tool parameters include a tool length, a tool tip diameter, a tool orientation, and a tool tip position, the tool tip position derived from one or more of a selected target position in the reconstructed images and a robot returned tip position determined based on feedback from a robotic system coupled to the x-ray system.

In this way, by determining the reconstruction error for the interventional tool, accuracy of assessment of tool position in the reconstructed images may be improved. Consequently, efficiency and accuracy of the interventional procedure may be increased, and patient care may be improved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 4 shows an example set of data tables including reconstruction error data, according to an embodiment of the disclosure;

DETAILED DESCRIPTION

Figure 1A:
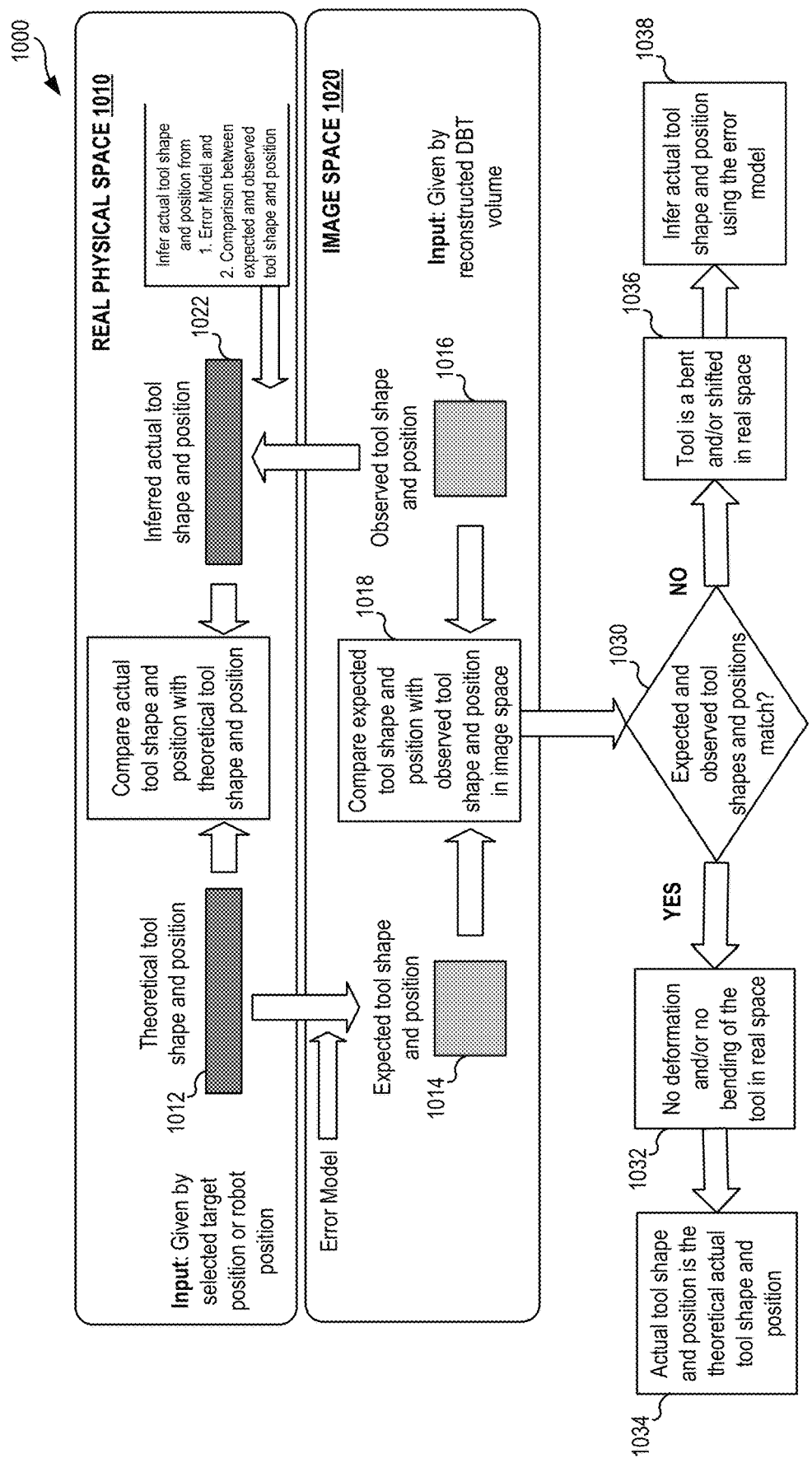
FIG. 1A is a high-level block diagram illustrating a schematic for evaluating a tool position within a tissue, according to an embodiment of the disclosure.

The following description relates to various embodiments for Digital Breast Tomosynthesis (DBT) guided interventional procedures. DBT is an imaging technique for generating cross-sectional images of breast at high in-plane resolution. DBT may be performed by utilizing an x-ray mammography system. Specifically, during DBT, the breast is compressed and an x-ray source may be rotated around the breast within a range of angles in positive and negative directions from a medial position, and low dose x-ray projection images of the breast at each angle may be obtained at a detector. The projection images are then reconstructed as slice images of breast volume along the z-direction. The range of rotation of the x-ray system for DBT may vary depending on the manufacturing configuration, and may be around a range of approximately ±11 degrees to ±60 degrees. The range of rotation of the x-ray system is also referred to as angular range of the x-ray system. A resolution of the reconstructed images along the direction of z-axis of the imaging volume may be based on the angular range. For example, for a DBT system with narrower angular range, the z-resolution may be lower.

During the DBT guided interventional procedures, tomosynthesis reconstructed images of the concerned breast are first obtained, and a target location (e.g., location of a lesion) within a region of interest (ROI) is identified by the user. An interventional tool and a biopsy gun like interventional tool holder of an interventional device are then adjusted such that when the interventional tool is inserted, the interventional tool is at a desired pre-fire position with respect to the selected target location. With the interventional tool inserted, another set of tomosynthesis images may be reconstructed to evaluate a current location of the interventional tool with respect to the target location. However, due to limited angular range of the x-ray system, the in-depth resolution of tomosynthesis along the z-direction is low. Particularly, when the interventional procedure is performed in a vertical approach, where the interventional tool is inserted vertically into the breast (for example, to obtain a portion of the concerned tissue), the resolution of the interventional tool in the reconstructed images along the z-direction is low, and thus leads to reconstruction error of the interventional tool in the tomosynthesis images. An example reconstruction error of the interventional tool is "leaking" in the z-direction. For example, the tool may be visible in a greater number of reconstructed image slices erroneously indicating a greater tool depth when the actual tool depth may be lesser. This leaking phenomenon may lead to difficulty in identifying the actual tool tip position, which is used to determine the relationship of the tool in the pre-fire position with respect to the target location. More generally, it is important for the success of the procedure to be able, at any step, to retrieve the actual tool tip position used to determine if the tool is correctly positioned in regards to target position.

The inventors herein have identified the above-mentioned issues, and have further identified that the reconstruction error is based on one or more tool parameters and target location parameters, in addition to acquisition system angular rotation. Accordingly, methods and systems are provided herein to address at least some of the issues discussed above. In one example, a method for an x-ray system, comprises: performing a digital breast tomosynthesis scan on a compressed breast with the x-ray system and generating tomosynthesis scan data; reconstructing images of the compressed breast from the tomosynthesis scan data; and determining an expected reconstruction error for an interventional tool based on an error model modelled as a function of selected target position from the reconstructed image, an angular range of rotation of the x-ray system, and interventional tool parameters.

In this way, before inserting the tool, the expected reconstruction error may be determined based on the error model as a function of one or more of tool parameters, location parameters, and acquisition system parameters. Further, the reconstruction error may be provided to the user, who can then determine if the reconstruction error is acceptable or if a different interventional tool should be used for the biopsy. Assessment of reconstruction error of the interventional tool and determination of actual tool tip position may improve the accuracy of interventional procedure, and reduce the number of repeats of procedure that may need to be performed to obtain the target tissue.

Further, upon selecting the tool, and moving the tool to a pre-fire position, pre-fire tomosynthesis images with the tool in the pre-fire position may be obtained. Based on an observed tool volume in the pre-fire images and an expected tool volume determined from the error model, an amount of bend of the tool tip during insertion may be determined. For example, during tool insertion to the pre-fire position, the tool trajectory may not be linear, and thus the tool tip may not reach the desired pre-fire position. A comparison of the expected tool volume and the observed tool volume may indicate if the tool has moved from its target path during the insertion. Further, when there is no bending, the observed tool volume and the expected tool volume are expected to match (that is, the volumes have a high degree of overlap).

Furthermore, based on an observed leaking of the tool (from the observed tool volume) and an expected leaking of the tool (from the expected tool volume) in the reconstructed volume, an actual position of the tool tip in a DBT volume may be determined. The determination of the actual tool tip may enable the user to evaluate the actual position of the tool tip with respect to the target lesion position, and further determine if the tool is positioned within at a desired position such that when fired, the tool penetrates the target tissue.

In addition to evaluating the tool tip position at the pre-fire stage, the error model may be utilized to evaluate the tool tip position at the post-fire stage after the tool is fired. For example, post-fire tomosynthesis images with the tool in the post-fire position may be obtained, and based on an observed tool volume in the post-fire images and an expected tool volume determined from the error model, the tool tip position at the post-fire stage may be evaluated.

Turning to FIG. 1A, a block diagram illustrating a high-level schematic 1000 for evaluation of an interventional tool position within a tissue, such as a compressed breast tissue, during a DBT-guided interventional procedure, is shown. Specifically, the schematic 1000 illustrates inferring an actual tool position in a real physical space 1010, such as a physical volume of a compressed tissue between a compression paddle and a detector surface, of an x-ray system such as the x-ray system 100 of FIG. 1B. The schematic 1000 is described with regard to the systems and components of FIGS. 1B, 1C, and 1D, although it should be appreciated the processes in the schematic may be implemented with other systems and components without departing from the scope of the present disclosure.

The interventional tool may be a mammography interventional tool such as a biopsy needle, a hook wire, an ablation needle, etc. During an image-guided mammography interventional procedure, such as a DBT-guided biopsy, hook wire localization, cryoablation, etc., it is desirable to evaluate an actual position of the tool in the real physical space so as to determine a positional relationship of the tool with respect to a target tissue to be extracted. As described above, when imaging the tool within the tissue, particularly with DBT, due to low resolution of image reconstruction in the z-direction (resulting from limited angular range of the x-ray source rotation), the tool appears in greater number of image slices (z-plane slices) than in the actual physical space, and as such, actual tool position may need to be inferred.

An exemplary theoretical tool shape and position is indicated at 1012. In one example, the theoretical tool shape and position may be determined based on one or more inputs. In one example, the theoretical tool shape and position may be determined from a user input. For example, based on the user clicking a desired portion on an image slice from a first plurality of DBT images of the tissue (with or without tool), spatial coordinates ($X_{target}$, $Y_{target}$, $Z_{target}$) of the target may be obtained. The coordinates may be utilized to determine the theoretical tool position and shape within the real physical space 1010. An exemplary determination of the target position coordinates is discussed below at FIG. 7C. In another example, a position feedback from a robotic system (referred to herein as robot returned tip position) of the interventional tool within the tissue may be utilized to obtain the theoretical tool position and shape. For example, during biopsy, a biopsy needle holder control system may also compute a needle tip position based on sensor data from a robotic system coupled to the biopsy needle holder control system. An example determination of the robot returned tip position is discussed at FIG. 8. In yet another example, when a smart tool is utilized, one or more sensors within the tool may return the tool position within the tissue on demand.

The theoretical tool shape and position 1012 may then be utilized to compute an expected tool shape and position 1014 in an image space 1020. The image space 1020 is the reconstructed DBT volume obtained from plurality of reconstructed images from the DBT acquisition. Thus, the theoretical tool shape and position 1012 may be utilized to evaluate how the tool would appear (location and shape) in the reconstructed DBT image volume. In particular, an error model, such as the error model 360 discussed with respect to FIG. 3B, may be utilized to compute the expected tool shape and position in the image space 1020. The error model may be stored in a memory of an imaging processor of the x-ray system, and based on one or more of a tool diameter, a tool length, the theoretical tool shape and position, source-to-image distance and acquisition system range, the error model may estimate an expected reconstruction error of a reconstructed tool image. The expected tool shape and position is then computed based on the expected reconstruction error. In this way, the expected tool shape and position are computed from the theoretical tool shape and position and the error model.

The expected tool shape and position, and the expected reconstruction error calculated from the error model may be determined prior to inserting the intervention tool into the tissue, and the expected reconstruction error, the expected tool shape and position, may be provided to a user, via a display portion of a user interface of the x-ray system, for example. Further, one or more interventional tools that may produce a smaller reconstruction error than the current selected interventional tool may be provided to the user via the interface. The one or more interventional tools with the smaller expected reconstruction error may be selected from an interventional tool reconstruction error database, such as data table shown at FIG. 4. The user may then utilize the expected reconstruction error to determine whether to proceed with the current selected interventional tool, or utilize a different tool that has a lesser reconstruction error.

Further, after the tool is inserted into the tissue, an observed tool shape and position 1016 may be determined from the DBT reconstructed image volume of the tissue with the tool. For example, with the tool positioned within the tissue, a tomosynthesis scan may be performed to obtain a second plurality of DBT images of the tissue with the tool positioned within. The observed tool shape and position 1016 may then be determined from the DBT reconstructed volume obtained from the second plurality of DBT images.

The expected tool shape and position 1014 in the image space 1020 and the observed tool shape and position 1016 in the image space 1020 are compared (as indicated at 1018) with the image processor. In one example, visual image processing descriptors may be utilized to compare the expected tool shape and position 1014 and the observed tool shape and position 1016 in the image space 1020.

Next, the processor may evaluate if the expected and the observed tool shapes and positions match (as indicated at 1030). If the theoretical tool shape is the same as the expected tool shape, and if the theoretical tool position is the same as the expected tool position (that is, answer at 1030 is YES), it may be determined that during the insertion of the tool into the tissue, no deformation or bending of the tool has occurred (as indicated at 1032). However, if the theoretical tool shape or position do not match the expected tool shape or position (that is, answer at 1030 is NO), it may be determined that the tool has bent and/or shifted in real space during insertion/movement within the tissue (as indicated at 1036).

If the comparison indicates that there is no deformation or bending of the tool during the insertion/movement of the tool within the tissue, the error model (and thus, the expected tool shape and position) may be utilized to inferred the actual tool position and shape within the tissue (that is, the actual tool position and shape in the real physical space), as indicated at 1034.

If the comparison indicates that the tool has bent and/or shifted in space, the expected tool shape and position may be compensated for bending (e.g., the expected tool shape and position may be compensated to match the observed tool shape and position). The actual tool shape and position may then be inferred from the compensated expected tool shape and position, and the error model, as indicated at 1038.

The inferred tool shape and position 1022 (either from 1038 or 1034) may then be compared with the theoretical tool shape and position (as indicated at 1040) to evaluate if the inserted tool is at a desired position with respect to the target tissue position.

In this way, the error model along with the expected and observed tool shape and position, may be utilized to evaluate an actual shape and position of the tool within the tissue.

In the following description, exemplary embodiments of the present invention are described with respect to a biopsy procedure as an exemplary interventional procedure, using biopsy needle as an exemplary interventional tool. It should be noted that the present invention may be implemented with respect to other interventional procedures and the respective interventional tools. The interventional procedures may include but are not limited to hook wire localization and cryoablation procedures. The interventional tools may include but not limited to hook wires utilized for hook wire localization, and probes utilized for cryoablation.

Figure 1B:
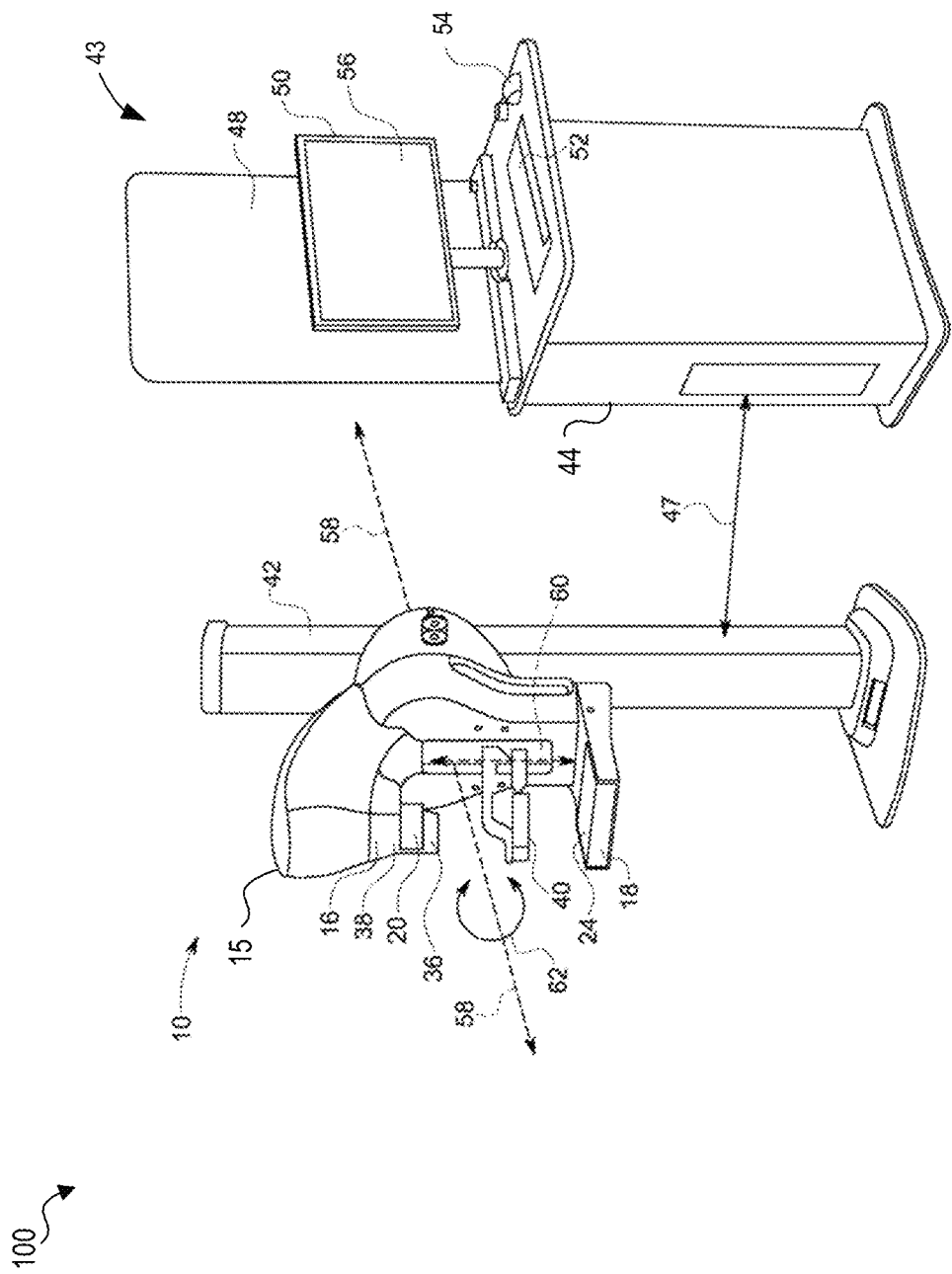
FIG. 1B is a schematic illustration of a mammography system for performing Digital Breast Tomosynthesis (DBT), according to an embodiment of the disclosure.
Figure 1C:
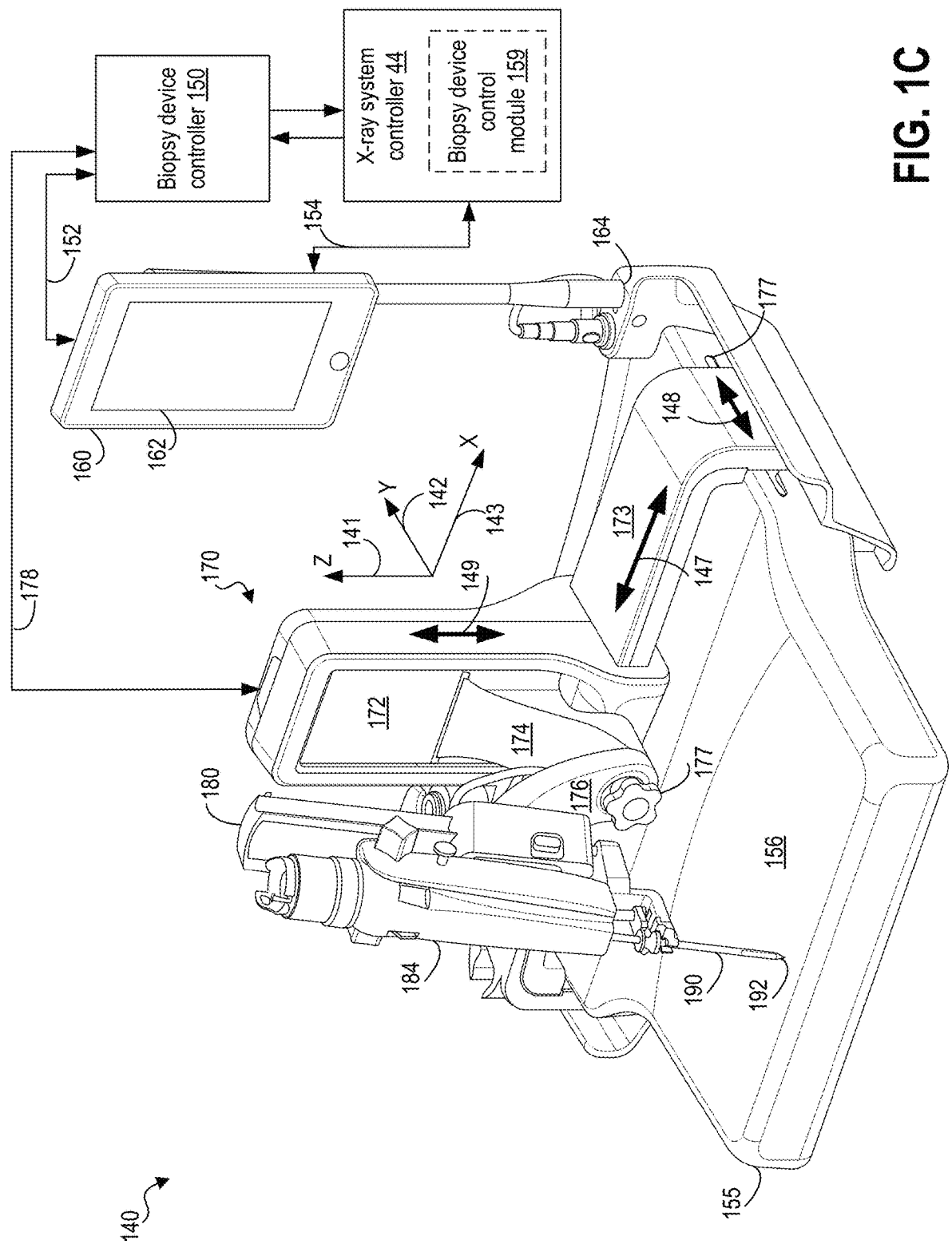
FIG. 1C is schematic illustration of a biopsy device that may be used in conjunction with the mammography system of FIG. 1B, according to an embodiment of the disclosure.
Figure 1D:
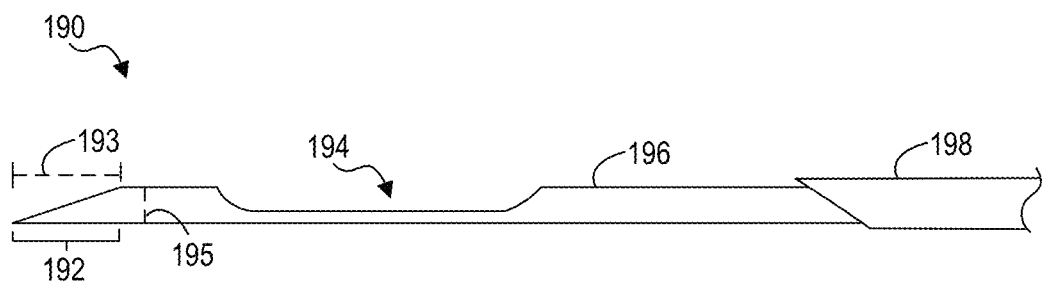
FIG. 1D is a schematic illustration of a biopsy needle that may be used in conjunction with the biopsy device of FIG. 1C, according to an embodiment of the disclosure.
Figure 2:
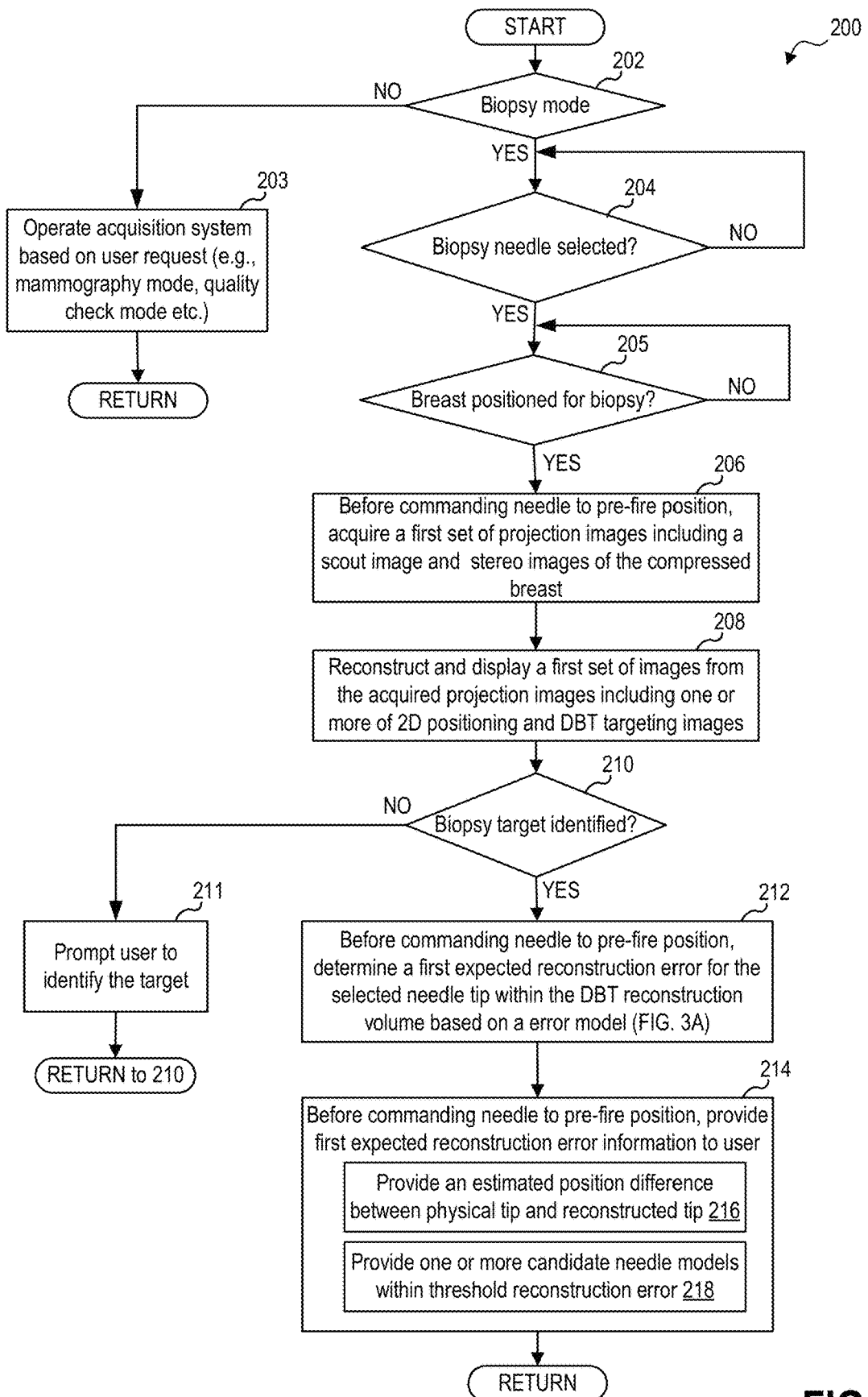
FIG. 2 is a high-level flow chart illustrating a method for selecting a biopsy needle for performing a DBT guided biopsy procedure; according to an embodiment of the disclosure.
Figure 5:
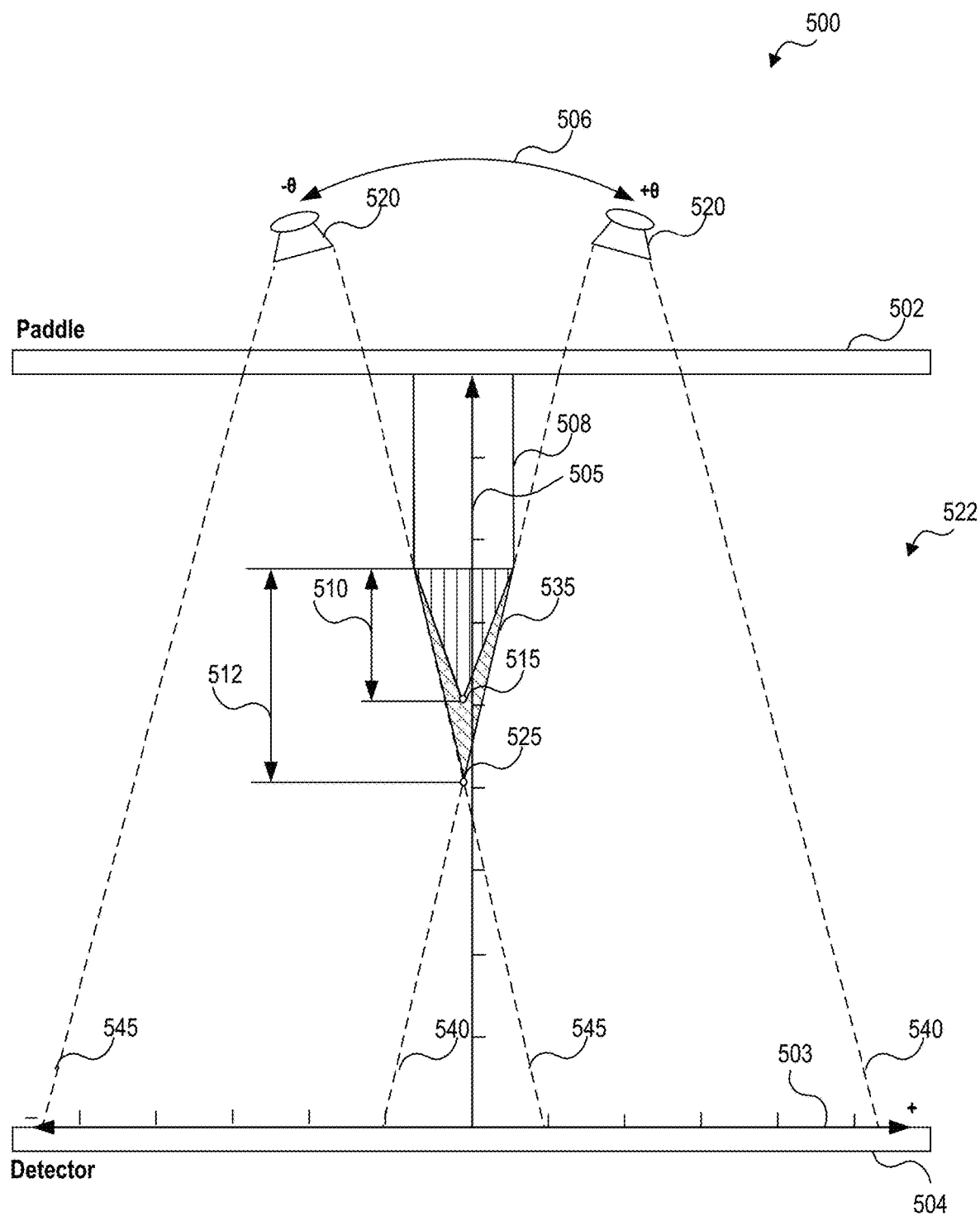
FIG. 5 is a schematic illustration of an example reconstruction error of a biopsy needle, according to an embodiment of the disclosure.
Figure 6:
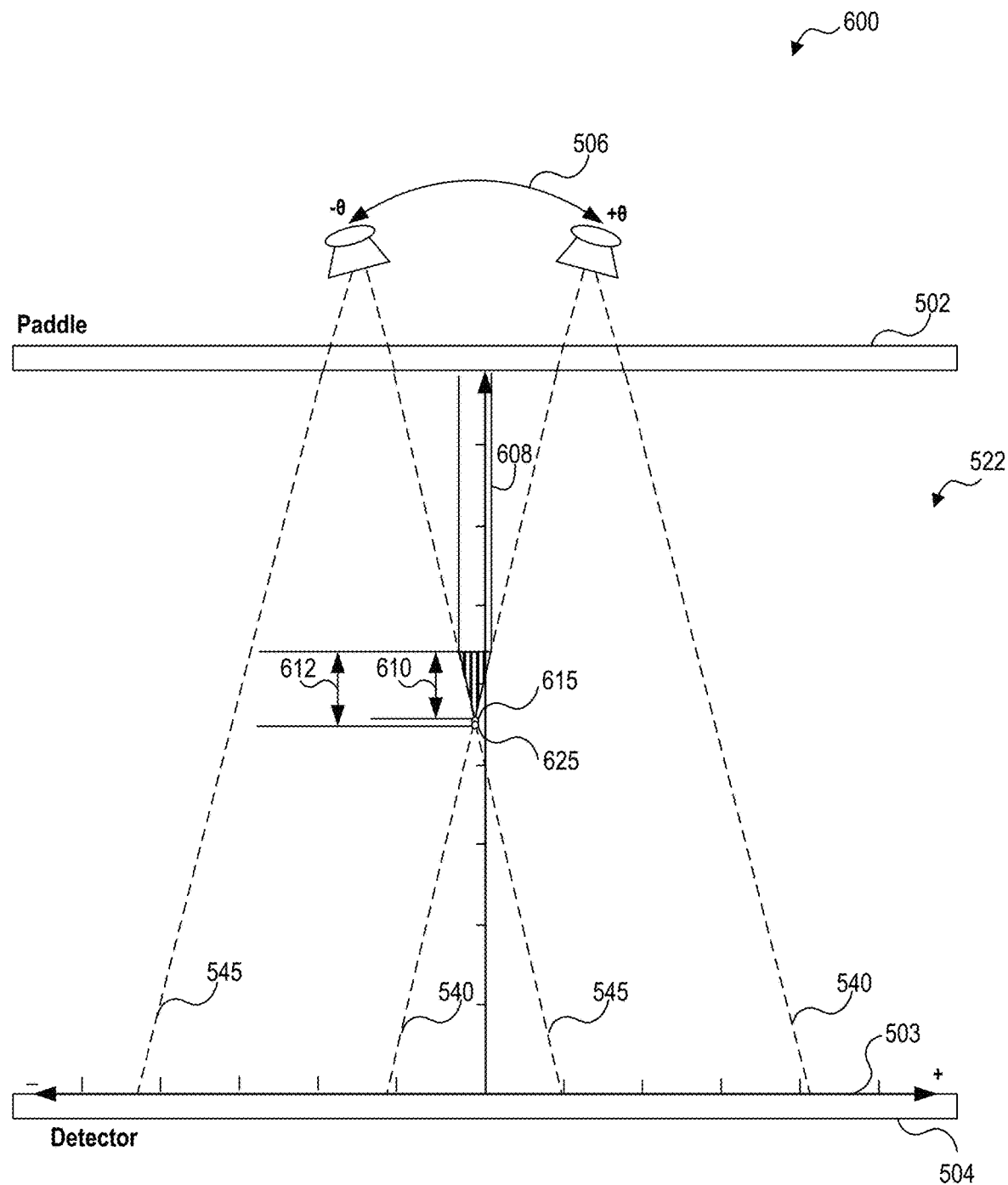
FIG. 6 is a schematic illustration of another example reconstruction error of a biopsy needle, according to an embodiment of the disclosure.
Figure 7A:
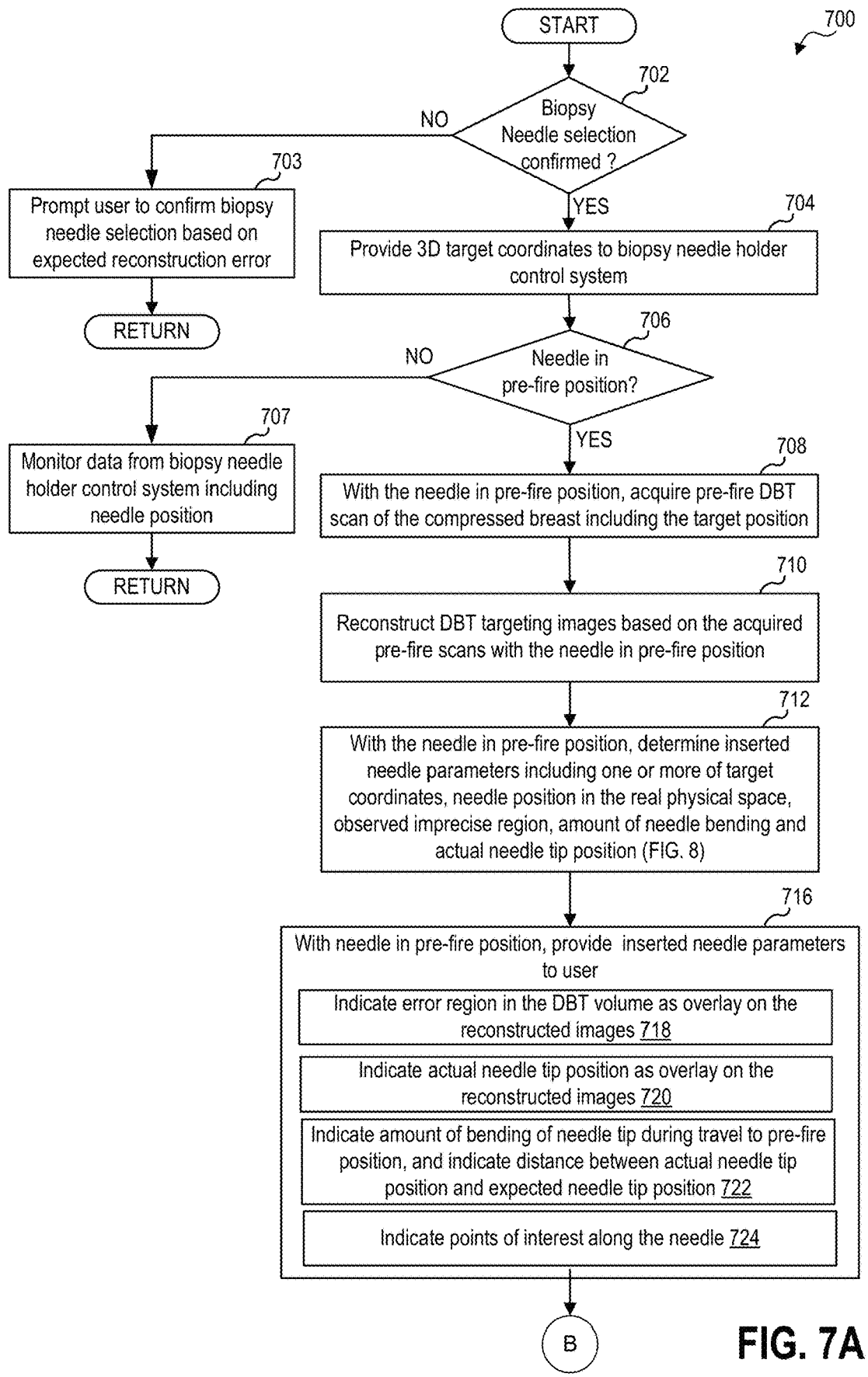
FIG. 7A is a high-level flow chart illustrating a method for performing a DBT guided biopsy procedure; according to an embodiment of the disclosure.
Figure 7B:
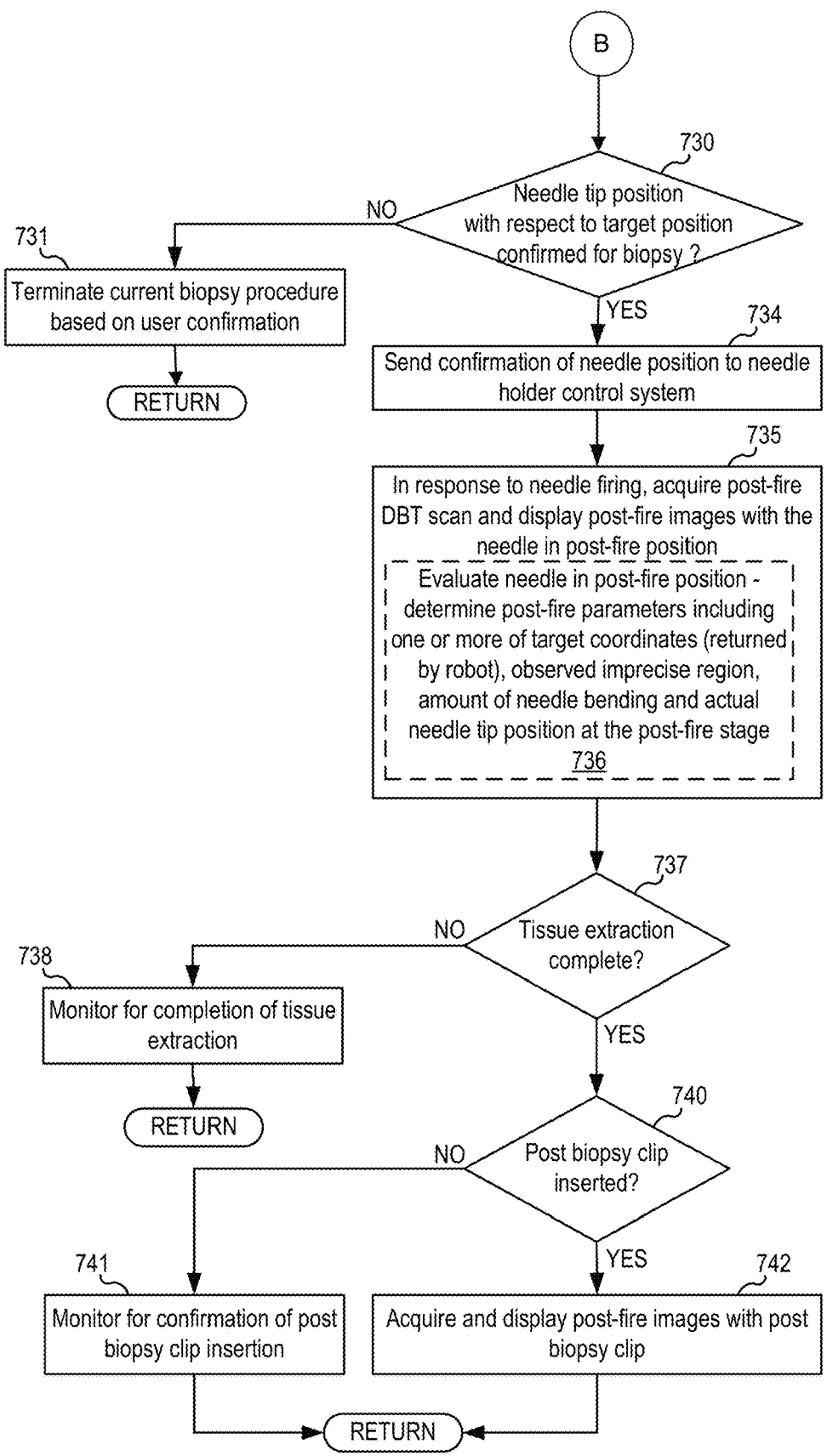
FIG. 7B is a continuation of FIG. 7A.

An exemplary x-ray system that may be used for DBT guided biopsy is shown at FIG. 1B. An exemplary biopsy device and biopsy needle that may be utilized for DBT guided biopsy are illustrated at FIGS. 1C and 1D. An example method for selecting a biopsy needle based on reconstruction error is shown at FIG. 2, and an example method for determining the reconstruction error and exemplary error model for determining reconstruction error before inserting the needle are described at FIGS. 3A and 3B. Briefly, a reconstruction error model is stored in a memory of an imaging processor of the x-ray system, and based on one or more of a needle diameter, a needle length, a target distance from the detector, and acquisition system geometry, the reconstruction error model may estimate an expected reconstruction error indicating an amount of leaking, in the z-direction, of a reconstructed needle image. Further, the reconstruction error model may be modelled such that an expected reconstruction error may be estimated for any type of interventional tool (e.g., hook wire, ablation needle, etc.) and/or various models of the same interventional tool type. The expected reconstruction error may be provided to the user before the needle is inserted into concerned tissue to the pre-fire position. Thus, the user may determine if the biopsy may be conducted with the current needle or a different needle may improve accuracy and efficiency of the biopsy procedure. In one embodiment, determining the expected reconstruction error for the biopsy needle may include utilizing a reconstruction error table. An example set of reconstruction error data table is shown at FIG. 4. Schematic illustrations of reconstruction errors for needles with different needle lengths and diameters are shown at FIGS. 5 and 6. Further, a high-level method for performing DBT guided biopsy using the expected reconstruction error to evaluate the needle position within the compressed breast is shown at FIGS. 7A and 7B. An exemplary selection of target position for biopsy from DBT reconstructed volume is discussed at FIG. 7C. Details of determining the one or more needle parameters, including the actual needle tip position and needle bending when the needle is inserted in the compressed breast is described at FIG. 8. An example schematic illustration of needle bending during insertion is shown at FIG. 9. It will be appreciated that the methods and systems described herein are applicable to evaluation of any position (pre-fire position, post-fire position, etc.) of any interventional tool (e.g., hook wire, ablation needle, ablation probe, biopsy needle, etc.) inserted in a tissue. Accordingly, a high-level block diagram for evaluating a tool position within a tissue is illustrated at FIG. 1A.

Referring to FIG. 1B, a mammography system 100 including an x-ray system 10 for performing a mammography procedure is shown, according to an exemplary embodiment. The x-ray system 10 may be a tomosynthesis system, such as a digital breast tomosynthesis ("DBT") system. Further, the x-ray system 10 may be used to perform one or more procedures including digital tomosynthesis imaging, and DBT guided interventional procedure, such as DBT guided breast biopsy. Further, the x-ray system 10 may be utilized to perform one or more of dual energy CESM, contrast enhanced DBT (CE-DBT) diagnostic, and interventional stereotactic procedures. Furthermore, the x-ray system 10 may be utilized to perform one or more image guided interventional procedures, including but not limited to image guided hook wire localization and image guided cryoablation.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about the axis 58. For example, the angular range of rotation of the radiation source 16 may be $-\theta$ to $+\theta$, where $\theta$ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged, and is configured to emit radiation rays at desired times and to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some exemplary embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1B, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Through its processors and controllers, the controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part. The controller 44 may also control how information, including images 42 and data acquired during the operation, is processed, displayed, stored, and manipulated. The different processing steps, including receiving one or more signals from one or more sensors, receiving user input, evaluating the received signals/input, image processing, determining reconstruction error, outputting operation parameters including error indications, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays mitted by the radiation source 16. In particular, during imaging with the x-ray system, a projection image of the imaging body part may be obtained at the detector 18. In some exemplary embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from $-\theta$ to $+\theta$, and a plurality of projection images of the compressed breast is obtained at various angles within the angular range. For example, if the angular range of the x-ray system is $\pm 11$ degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct a DBT volume rendering of the breast.

Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis. An exemplary biopsy device is illustrated at FIG. 1C.

Turning to FIG. 1C, a schematic illustration of a biopsy device 140 that may be used in conjunction with a mammography system, such as the mammography system 100 of FIG. 1B, is shown. The biopsy device 140 will be described herein with reference to the mammography system 100 at FIG. 1B. Biopsy device 140 includes a biopsy table 155 that is positioned over the detector 18 of the x-ray system 10. In one example, the biopsy table 155 may be configured to slide over the detector 18. During set-up of the biopsy device 140, the user may remove the compression paddle 40 of the x-ray system 10, and slide the biopsy table 155 over the detector 18. Upon positioning the biopsy device 140 on the x-ray system 10, a suitable compression paddle for biopsy (not shown), such as a horizontal paddle or vertical paddle, depending on the type of biopsy, may be selected and coupled to the x-ray system 10.

A biopsy device interface 160 having a biopsy device display 162 may be coupled to the biopsy table 155 via a communication port 164. In one embodiment, the biopsy device interface 160 may be communicatively coupled with the x-ray system controller 44, as indicated by double ended arrow 154, and as such, the user may be able to adjust a position of the x-ray system, such as adjusting the gantry to a park position, via the biopsy device interface 160. In other embodiments, the biopsy device interface 160 may be coupled to a biopsy device controller 150, which sends and receives information to and from the x-ray system controller 44 (as indicated by double ended arrow 152). In some other embodiments, additionally or alternatively, adjustment and control of the biopsy device 140 may be performed by a biopsy device control module 159 of the x-ray system controller 44.

Biopsy device 140 includes a biopsy tool system 170 that may be directly coupled to the biopsy table 155. The biopsy tool system 170 includes a robotic system comprising a trunk 172 to which a first arm 174 is attached. The biopsy tool system 170 may further include a second arm 176 that is coupled to the first arm 174 on one end and coupled to a biopsy gun holder 180 at a second opposite end. The second arm 176 may be pivoted with respect to the first arm 174 to adjust a position of the biopsy gun holder. The illustration in FIG. 1C shows the biopsy tool system 170 configured in a vertical approach for biopsy. The vertical approach involves inserting an interventional tool (e.g., a biopsy needle) into the breast in a direction perpendicular to a horizontal plane of the compression paddle. The interventional tool may be alternatively referred to as tool. It will be understood that the interventional tool (or the tool) may include but not limited to any of a biopsy needle, a hook wire, and an ablation needle/probe. Thus, during setting up the biopsy device 140 in the vertical approach, the biopsy gun holder 180 is positioned such that a longitudinal axis of the biopsy gun holder along a length of the biopsy gun holder is parallel to z-axis 141 and perpendicular to a horizontal surface 156 of the biopsy table 155.

The biopsy tool system 170 may be adjusted to perform biopsy in a lateral (also referred to as horizontal) approach where the needle is inserted into the breast in a direction parallel to the compression paddle. During setting up the biopsy tool in the lateral approach, the second arm 176 may be pivoted by 90 degrees, via a knob 177, such that the longitudinal axis of the biopsy gun holder is perpendicular to z-axis 141 and parallel to the horizontal surface of the biopsy table 155.

The biopsy gun holder 180 may be utilized for mounting a biopsy gun 184. Further, the biopsy gun holder 180 may include a mechanical stop for adjusting a position of a biopsy needle 190. Specifically, during biopsy, prior to inserting the interventional tool, the breast is positioned between a compression paddle (not shown) and surface 156. In some examples, a breast spacer may be positioned on the surface 156, and the breast is positioned between the compression paddle and the spacer, and compressed by moving the compression paddle toward the surface 156. Upon positioning the breast, a first set of targeting images are obtained by the scanning the compressed breast with x-ray system 10 at various angles over its angular range to identify a target for biopsy. The first set of targeting images may be three dimensional images (DBT images) or two-dimensional full field digital mammography images reconstructed from the x-ray system acquisitions. The user may localize the concerned region and identify a target position for biopsy by selecting the target position from the first set of DBT images. The target position may be identified by x, y, and z coordinates within a DBT volume between the compression paddle and the biopsy table surface 156 or spacer (if used). Based on the target position coordinates selected by the user, the biopsy device controller 150 may adjust the mechanical stop position of the biopsy gun holder 180 such that when the needle is inserted into the compressed breast via the biopsy gun 184, the needle movement is stopped when the needle tip reaches a desired position with respect to the target position. While the present example illustrates adjust of the biopsy device via the biopsy device controller 150, it will be appreciated that in some embodiments, the x-ray system controller 44 may command control of the biopsy device 140. In this way, during biopsy in the vertical approach mode, the depth position of the biopsy needle may be adjusted with the biopsy gun 184 and biopsy gun holder 180 by moving the first arm 174 upward and/or downward with respect to the trunk 172 to adjust the z-position and the mechanical stop position.

Further, the biopsy tool system 170 may include a platform 173 and a rail 177. The trunk 172 of the biopsy tool system 170 may move over the platform 173 parallel to x-axis 143. Movement of the biopsy tool system 170 over the platform 173 is indicated by double ended arrow 147. The movement of the trunk along the platform 173 may be adjusted by the controller. Thus, during biopsy, the position of the biopsy gun 184 and gun holder 180 may be adjusted along the direction of x-axis such that an x-axis coordinate of the tool position is adjusted with respect to the target position. Further, the platform 173 may move in a direction of y-axis 142 along the rail 177. Movement of the biopsy tool system 170 in the direction of y-axis is indicated by double ended arrow 148. Thus, during biopsy, the position of the biopsy gun and gun holder may be adjusted along the direction of y-axis such that a y-axis coordinate of the tool position is adjusted with respect to the target position. Furthermore, the biopsy tool 170 may move upward and downward, as indicated by double ended arrow 149. For example, the arm 174 may be movable in the direction of z-axis 141 indicated by arrow 149 to adjust a position of the biopsy gun holder 180 (and thus, the biopsy gun 184 and the biopsy needle 190) along the z-axis 141. The movement of the biopsy tool, in the x, y, and z directions may be adjusted by the controller 150. It will be appreciated that embodiments where the adjustment of the biopsy tool in one or more of the x, y, z, directions is performed manually in addition to or alternative to the adjustment by the controller are also within the scope of the disclosure.

Since manual adjustment is possible, when performing a DBT after adjusting the tool, the new tool tip location may be determined from the error model and observed leaking in the DBT volume, as further discussed below.

Taken together, during biopsy, upon selection of target position from the first set of targeting images obtained by the x-ray system, prior to inserting the needle 190, the controller (which may be x-ray system controller 44 or biopsy device controller 150), may adjust position of the biopsy needle by adjusting the biopsy tool in the direction 147 of x axis, in the direction 148 of y axis, and adjusting the mechanical stop position in the direction of z axis based on the target position coordinates such that when the needle is inserted the needle tip is at the desired position in the breast tissue with respect to the target position.

In this way, the robotic system of the biopsy tool system 170 may be utilized to adjust the needle position and biopsy tool position based on the target position computed from images.

Once the biopsy tool system 170 and the biopsy gun are at target position, the user/radiologist may drive the needle through the biopsy gun184 until it reaches the mechanical stop. Once fully inserted, the needle is then at the target position (that is, the position where a notch of the needle is in front of the lesion to puncture). An example illustration of a biopsy needle that may utilized for biopsy with the biopsy device 140 is shown at FIG. 1D.

Turning to FIG. 1D, a schematic illustration of an exemplary biopsy needle 190 is shown. The biopsy needle may include a needle tip region 192, an outer cannula 198, an inner cannula 196 positioned therein, and an opening (notch) 194 for receiving a portion of tissue from the biopsied lesion or target. The inner and outer cannulas form a cutting device wherein the outer cannula 198 is configured to slide or rotate over the inner cannula, and/or the inner cannula is configured to slide or rotate within the outer cannula. In one example, during biopsy, when the needle 190 is at the pre-fire position, an end of the needle tip 192 and the notch are above the target, and, when the needle 190 is at the post-fire position, the notch is in front of the target. When the pre-fire position of the needle is confirmed (that is, when the needle is at the desired position with respect to the target), the user may actuate (that is, fire) the biopsy gun to deploy the biopsy needle. When the biopsy needle is deployed (that is, when the biopsy needle is fired), the needle tip may pass through the target tissue followed by the notch and the inner cannula. When the inner cannula is inserted through the target tissue, a portion of the target tissue may settle onto the notch. Almost instantaneously, the outer cannula may move forward and incise the portion of tissue that had settled on the notch. A second set of post fire images may be obtained by the x-ray system with the needle 190 in the post-fire position. The incised tissue is then extracted from the needle via an assisted approach, such as vacuum assisted biopsy, and the needle is removed from the patient.

When the biopsy needle 190 is imaged in the DBT volume, due to limited resolution of the tomosynthesis images in the z-direction (that is the direction perpendicular to the biopsy table surface 156), the biopsy needle 190 appears to leak in the z-direction. Said another way, an artefact image of the biopsy needle 190 may be visible in additional image slices. As a result, an observed end of the needle tip in the images may be different from the actual end of the needle tip 192. This leaking of the needle tip in the z-direction may depend on a needle tip length 193 and a needle diameter 195 in addition to other parameters including target position and x-ray system parameters as further discussed below.

In one embodiment, a controller, such as controller 44 at FIG. 1B, may store an error model that may be utilized for calculating a reconstruction error in the reconstruction of images, including a biopsy needle image, from a tomosynthesis acquisition. The error model may be based on needle parameters including the needle length and needle diameter, a selected target position within the imaging volume, and x-ray system parameters. During breast biopsy procedures in a vertical approach, due to poor resolution of the DBT images in the z-direction, the biopsy needle appears in a greater number of image slices and thus, appears to be leaking in the z-direction. As such, when reviewing the DBT reconstructed images with the biopsy needle, it may be difficult to ascertain the actual needle tip position (and consequently, indirectly determine the notch position that may be of clinical interest), and determine if the needle is at the desired position with respect to the target position coordinates. Some of the above mentioned issues may be addressed by determining an expected reconstruction error for a given selected needle based on the error model. The expected reconstruction error may indicate an expected amount of leaking for the selected needle prior to inserting the needle for biopsy. Based on the expected leaking, the user may be informed of the expected reconstruction error even before beginning the biopsy procedure, and may be able to decide whether the expected reconstruction error is acceptable for a given biopsy procedure. Details of the error model and determination of reconstruction error prior to inserting the needle is described below with respect to FIGS. 2-6.

Further, the controller may store instructions for determining an actual needle tip position of the selected biopsy needle based on an observed needle volume in reconstructed images of the needle in one or more of a pre-fire position and a post-fire position, and the expected reconstruction error. Additionally, based on the observed needle volume and the expected reconstruction error, the controller may evaluate if the needle has bent during insertion to the pre-fire position and subsequently, to the post-fire position. Further, other areas of interest along the needle when the needle is at one or more of the pre-fire position and the post-fire position, such as notch position, may be determined based on the observed needle volume and the expected reconstruction error. Details of utilizing the expected reconstruction error during a DBT guided biopsy procedure are further described with respect to FIGS. 6-9.

In some exemplary embodiments, the controller may store an error model for an interventional tool that may be utilized for calculating a reconstruction error for an interventional tool in the reconstruction of images including the interventional tool image from a tomosynthesis acquisition. The error model for the interventional tool may be based on interventional tool parameters including an interventional tool length and interventional tool diameter, a selected target position within the imaging volume, and x-ray system acquisition parameters. During interventional procedures in a vertical approach, due to poor resolution of the DBT images in the z-direction, the interventional tool may appear in a greater number of image slices and thus, appear to be leaking in the z-direction. As such, when reviewing the DBT reconstructed images with the interventional tool, it may be difficult to ascertain the actual tool position, and determine if the tool is at the desired position with respect to the target position coordinates. Some of the above mentioned issues may be addressed by determining an expected reconstruction error for a given selected interventional tool based on the error model. The expected reconstruction error may indicate an expected amount of leaking for the selected interventional tool prior to inserting the interventional tool. Based on the expected leaking, the user may be informed of the expected reconstruction error even before beginning the interventional procedure, and may be able to decide whether the expected reconstruction error is acceptable for a given interventional procedure.

Further, the controller may store instructions for determining an actual tool position of the selected interventional tool based on an observed tool volume in reconstructed images of the interventional tool in one or more of a pre-fire position and a post-fire position, and the expected reconstruction error for the selected interventional tool. Additionally, based on the observed tool volume and the expected reconstruction error, the controller may evaluate if the tool has bent during insertion into the tissue. Further, other areas of interest along the tool may be determined based on the observed tool volume and the expected reconstruction error.

Next, FIG. 2 shows a high-level flow chart illustrating an example method 200 for selecting a biopsy needle for DBT-guided biopsy with an x-ray imaging system, such as x-ray system 10 at FIG. 1B, and a biopsy device, such as biopsy device 140 at FIG. 1C. Method 200 may be implemented by an image processing system, such as controller 44 at FIG. 1B, an edge device connected to the image processing system, a cloud in communication with the image processing system, or any appropriate combination thereof. Method 200 is described with regard to the systems and components of FIG. 1B and FIG. 1C, although it should be appreciated that method 200 may be implemented with other systems and components without departing from the scope of the present disclosure. Further, it will be appreciated that the method 200 may be utilized for selecting an interventional tool including but not limited to a biopsy needle, a hook wire, and an ablation needle/probe depending on the interventional procedure (e.g., biopsy, hook wire localization, cryoablation, etc.) performed with the x-ray system.

Method 200 begins at 202. At 202, method 200 includes determining if the x-ray system is operated in a biopsy mode. The biopsy mode operation may be determined based on detecting the biopsy device coupled to the x-ray system. During a set-up operation for a biopsy procedure, the biopsy device may be positioned over the detector of the x-ray system by sliding a biopsy table, such as biopsy table 155, over the detector, for example. Further, a biopsy device interface, such as interface 160 at FIG. 1C, may be coupled to the x-ray system. In one example, the biopsy device may be automatically detected when one or more of the biopsy device and the biopsy device interface are coupled to the x-ray system. In another example, a user may indicate via a user interface of the x-ray system that the biopsy device is coupled to the x-ray system, and the x-ray system is in the biopsy mode of operation.

If biopsy mode is confirmed, the answer at 202 is YES, and method 200 proceeds to 204. At 204, method 200 includes determining if a biopsy needle is selected for the biopsy procedure. For example, the user may select a desired biopsy needle from a set of prescribed biopsy needles based on one or more of patient parameters, target tissue parameters, biopsy device parameters, and x-ray system parameters. The user may then indicate the selection of the desired biopsy needle and a type of the desired biopsy needle selected via a user interface, such as the biopsy device interface or the x-ray system interface. While the above example describes biopsy needle selection, it will be appreciated that an interventional tool may be selected based on the interventional procedure performed with the x-ray system. The interventional tool may include but not limited to a hook wire for hook wire localization and an ablation needle for cryoablation. Accordingly, in some embodiments, at 202, the method 200 may include determining a type of interventional procedure (e.g., hook wire localization, cryoablation, etc.) and at 204, the method 200 may include determining if a corresponding interventional tool (e.g., hook wire, ablation needle etc.) is selected for the interventional procedure.

In some embodiments, the user may mount the desired biopsy needle onto a biopsy gun, such as biopsy gun 184 at FIG. 1C. In such cases, the presence of the biopsy needle may be determined based on sensing of the biopsy needle by one or more sensors coupled to one or more of the biopsy holder and the x-ray system. An example sensor system may include a computer vision system. Other types of sensors for sensing the loading of the biopsy needle and the presence of the biopsy needle in the biopsy holder are also within the scope of the disclosure.

If the selection of the biopsy needle is not confirmed, the answer at 204 is NO, and method 200 continues to monitor for biopsy needle selection. It will be appreciated that, in some examples, upon confirming the biopsy mode, method 200 may proceed to 205, and the needle selection and/or loading may be confirmed at a later step, before commanding any needle movement.

If the desired biopsy needle is selected, the answer at 204 is YES, and method 200 proceeds to 205. At 205, method 200 includes, determining if a body part, such as a breast, is positioned for biopsy. Prior to a breast biopsy procedure, the breast is compressed with a compression paddle to reduce movement during the biopsy. When a desired immobilization is achieved, the user may indicate via the x-ray system user interface and/or the biopsy device interface that the breast is in position for imaging. As such, determination of whether the breast is in position may be based on the user indication. In some examples, one or more sensors (e.g., vision sensors) coupled to the x-ray system and/or the biopsy device, may be utilized to determine if the breast is positioned for imaging.

If the breast is not positioned for imaging, the answer at 205 is NO, and method 200 proceeds to monitor positioning of the breast. If the breast is positioned for imaging, the answer at 205 is YES, and method 200 proceeds to 206. At 206, method 200 includes acquiring a first set of projection images at various angles within the angular range of the x-ray system. In particular, before commanding the biopsy needle to a pre-fire position, the x-ray system may perform a first tomosynthesis scan with the x-ray system to generate the first set of projection images of the compressed breast at the detector. The first set of projection images may include a scout image (obtained with the x-ray tube positioned at zero degrees from a midline axis perpendicular to the top surface of the detector) and plurality of projection images at various angles within the angular range of the x-ray system. For example, if the angular range of the x-ray system is 22 degrees, the x-ray system may acquire the first set of projection images with the x-ray tube at various angles ranging between −11 degrees from the midline and +11 degrees from the midline. During image acquisition based on DBT, at each angulation of the x-ray system over the angular range, a cone beam of low dose x-ray radiation from the x-ray tube may pass through the compressed breast, and is projected onto the detector to obtain a projection image.

Upon obtaining the first set of projection images, method 200 proceeds to 208. At 208, the first set of projection images from the detector are reconstructed into slices of volume of breast, each with an amount of thickness (e.g., 1 mm) to obtain a first set of reconstructed images, and displayed on the user interface of the x-ray system. The first set of images are tomosynthesis reconstructed images, and may be displayed on a user interface in a sequential loop at a desired rate, which may alternatively be viewed one by one based on user preference. In this way, by moving the x-ray tube over the angular range, capturing a plurality of projection images of the breast at various angles within the angular range, and reconstructing the plurality of projection images into plurality of slices through the volume of breast in the z-direction, the first set of reconstructed images (before inserting the biopsy needle into the compressed breast) may be obtained.

Next, at 210, method 200 includes determining if a biopsy target location for biopsy is selected. The target location for biopsy may be within a region of interest and may be selected by the user, via the x-ray system user interface and/or the biopsy device interface, based on identification of an abnormality from the first set of reconstructed images. The abnormality may be an indication of breast cancer and may include one or more of lesion, microcalcification, architectural distortion, and any deviation from normal breast anatomy that may be an indication of breast cancer. The user may select the target by highlighting the target location, for example. The target location may be alternatively referred to herein as the target position. While the above example describes a biopsy target location, it will appreciated that the target location may be selected for any image-guided interventional procedure, such as hook wire localization, cryoablation etc.

If the biopsy target position is not identified, the answer at 210 is NO, and method 200 proceeds to 211. At 211, method 200 includes prompting the user to identify the target. Method 200 may then return to step 210 to determine if the biopsy target has been selected. If the biopsy target position is identified, the answer at 210 is YES, and method 200 proceeds to 212. At 212, method 200 includes determining a first expected reconstruction error for the selected biopsy needle within an entire DBT reconstruction volume. The entire DBT volume may include each of the individual volume slices of the first set of reconstructed images. In particular, the first expected reconstruction error may be determined based on an error model. The error model is based on selected needle parameters, the selected biopsy target location, and the x-ray system parameters. It may be noted that the error model may be implemented for any selected interventional tool including but not limited to a hook wire, ablation needle, biopsy needle, etc. As such, the error model may be based on selected interventional tool parameters, a selected target location for a desired interventional procedure, and the x-ray system parameters. Details of determining the first expected reconstruction error based on the error model is described further with respect to FIGS. 3A and 3B.

Figure 3A:
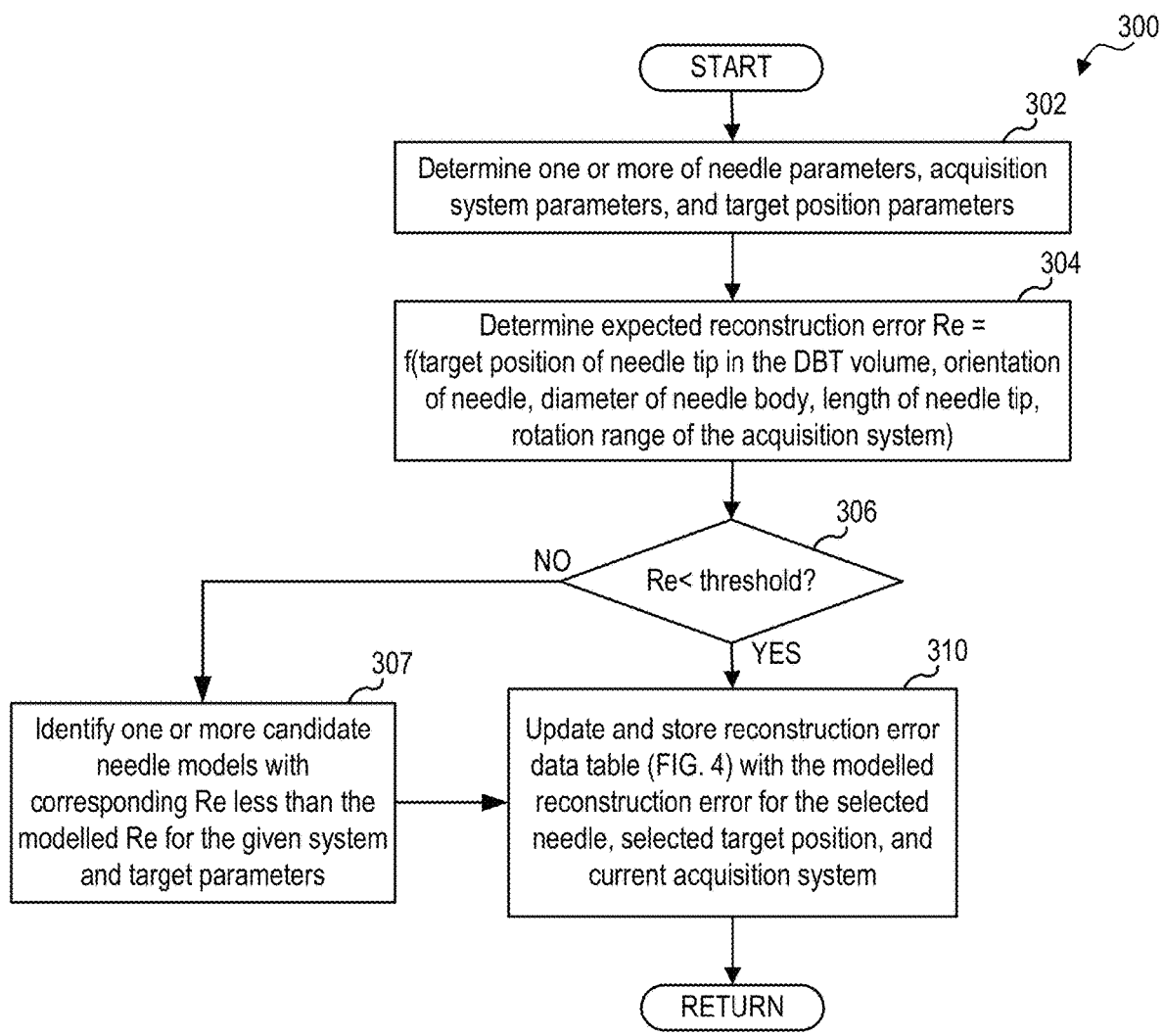
FIG. 3A is a high-level flow chart illustrating a method for determining biopsy needle reconstruction error prior to performing a DBT guided biopsy procedure; according to an embodiment of the disclosure.

Turning now to FIG. 3A, a high-level flowchart illustrating a method 300 for determining the expected reconstruction error in the image reconstruction of the needle during DBT guided biopsy. Method 300 may be implemented by an image processing system, such as controller 44 at FIG. 1, an edge device connected to the image processing system, a cloud in communication with the image processing system, or any appropriate combination thereof. Method 300 is described with regard to the systems and components of FIGS. 1B, 1C, and 1D, although it should be appreciated that method 300 may be implemented with other systems and components without departing from the scope of the present disclosure. In an exemplary embodiment, method 300 may be implemented by a biopsy holder controller in communication with the image processing system.

As described above, during DBT imaging, the x-ray system is rotated within the angular range of the x-ray system to acquire plurality of projection images, which are subsequently reconstructed into plurality of 3D slices of the breast volume. Due to lack of complete rotation (360 degrees) of the x-ray system during DBT, the DBT reconstructed images have poor resolution in the z-direction, resulting in reconstruction error that may cause the biopsy needle to be visualized in more number of planar slices of breast volume than in the actual planes. Said another way, the needle may appear to be greater in length in the reconstructed images than an actual needle length. Consequently, when the needle is inserted into the breast, the reconstruction error may cause the needle tip to appear at a different location than the actual needle tip position. As a result, the user is unable to determine if the needle tip is within a threshold error distance from the target location for biopsy. By determining the reconstruction error before inserting the needle, the user may be able to evaluate if the expected reconstruction error is acceptable or not. Method 300 illustrates determination of the expected reconstruction error even before the needle is inserted into the compressed breast. Method 300 may be initiated upon selecting the target biopsy location from the first set of reconstructed images and the biopsy needle, and prior to commanding movement of the needle to the pre-fire position. Further, it will be appreciated that the method 300 may be implemented for determining a tool expected reconstruction error in the image reconstruction of an interventional tool including but not limited to a biopsy needle, a hook wire, and an ablation needle/probe depending on the interventional procedure (e.g., biopsy, hook wire localization, cryoablation, etc.) performed with the x-ray system.

Method 300 begins at 302. At 302, method 300 includes determining one or more of selected needle parameters, selected biopsy target location parameters, and acquisition system parameters. Needle parameters may include an orientation of the selected needle (e.g., vertical, horizontal, or oblique (and desired oblique angle if the orientation is oblique)), a diameter (such as diameter 195 at FIG. 1d) of a body portion (such as inner cannula 196 at FIG. 1D) of the selected needle, and a tip length (such as length 193 of the needle tip 192 at FIG. 1D) of the selected needle. The needle parameters may be specific to the needle selected. In one example, the user may indicate the type of needle selected via one or more of the biopsy device user interface and the x-ray system user interface, and the needle parameters may be determined by the controller from the specification of the selected needle stored in non-transitory memory of the controller. It will be appreciated that determination of needle parameters based on one or more sensors coupled to one or more of the biopsy device and the x-ray system, are also within the scope of the disclosure.

Selected biopsy target location parameters may include an expected tip position along the z-direction when the needle is inserted in the compressed breast. That is, an expected depth position of the needle tip along the z-direction perpendicular to detector plane may be determined based on the selected biopsy target location. As an example, during a vertical biopsy approach, when the desired needle movement is downward toward the detector plate along the z-axis, a needle pre-fire position may be slightly above the target location along the z-axis such that when fired, the needle tip passes through the target location to collect the target tissue at the notch for analysis. Thus, the expected tip position (and consequently, the expected notch position with respect to the target location based on the expected tip position and the needle parameters) along the z-axis in the pre-fire position may be determined based on the selected target location from the first set of reconstructed images. In some examples, selected target location parameters may include x, y, and z coordinates of the target location.

Acquisition system parameters includes the acquisition system geometry that includes the angular range of rotation of the x-ray acquisition system, one or more focal spot parameters (position and size), and a source-to-image distance (that is, distance from the focal spot (at which the x-rays are generated) to a detection surface of the detector). For example, the angular range of the x-ray system in one direction from the medial (zero degrees) may vary between ±11 and ±60 degrees depending on the manufacturer. While the above example illustrates a range between 11 and 60 degrees based on current manufacturing capabilities, it will be appreciated that x-ray systems with the angular range below ±11 degrees and above ±60 degrees are also within the scope of the disclosure.

Next, method 300 proceeds to 304. At 304, method 300 includes determining the expected reconstruction error (Re) based on an error model constructed as a function of an expected position of needle tip in the DBT volume, orientation of needle, diameter of needle body, length of needle tip, and rotation range of the acquisition system. Specifically, the reconstruction error increases as the needle is more vertically oriented. Further, the reconstruction error increases with increase in needle diameter. Furthermore, as the tip position in the DBT volume approaches closer to the detector, the reconstruction error increases. Further still, when the angular range of the acquisition system decreases the reconstruction error increases.

Figure 3B:
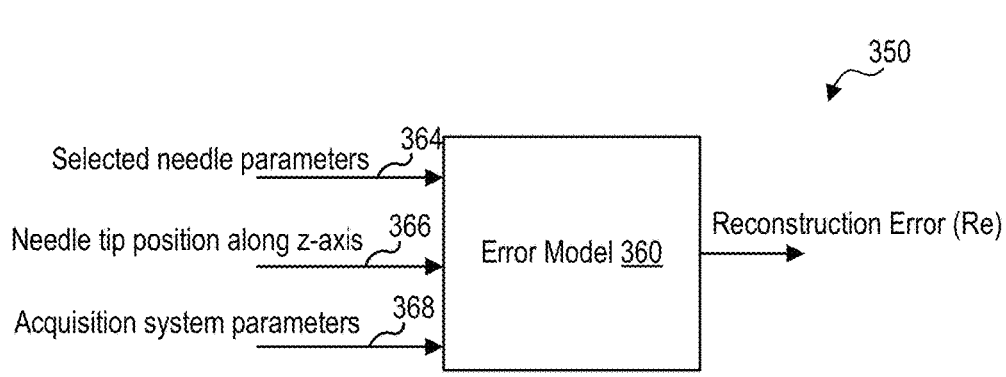
FIG. 3B is a block diagram illustrating an error model for determining a reconstruction error, according to an embodiment of the disclosure.

In one example, the expected reconstruction error may be computed based on the error model depending on the selected needle parameters, the selected target location, and the acquisition system parameters as shown in FIG. 3B. Turning to FIG. 3B, a block diagram 350 of an error model 360 according to an exemplary embodiment is illustrated. The error model 360 uses as input selected needle parameters 364 (length, diameter, and orientation), a needle tip position along the z-axis 366 (based on the selected target position from the first set of reconstructed images), and acquisition system parameters 368 (angular range). The error model provides as output the expected reconstruction error Re.

In another example, a reconstruction error data set including reconstructed error data determined at various distances from the detector for a given set of needle types (each with specific needle length and diameter) for a given x-ray system may be stored in the non-transitory memory of the controller. In one example, the reconstructed error data set may be based on the error model as discussed above. In another example, the reconstruction error data set may be based on evaluating observed reconstructed tip length in air at specific distances along the z-axis for each needle model. The observed reconstructed tip length may be compared with the actual position of the needle tip in air to determine the reconstruction error of each needle model. In this way, the reconstruction data set may be built and stored. During DBT guided biopsy, prior to commanding any movement of the needle through the compressed breast tissue, based on the selected needle type and the selected target location, the first expected reconstruction error may be determined from the reconstruction error dataset. An example set of tables with reconstruction error data, which may be stored in the memory of the image processor, is described at FIG. 4.

Turning to FIG. 4, an example set of reconstruction error data tables is shown. Specifically, a first data table 400 and a second data table 450 are illustrated. The first data table 400 and the second data table 450 include reconstruction error data for biopsy needles determined based on an error model, such as the error models discussed with respect to FIGS. 3A and 3B above.

In some examples, the reconstruction error data for biopsy needles may be determined by obtaining tomosynthesis projection images of various biopsy needle models in air at a plurality of distances from the detector in the DBT volume between the compression paddle and the detector. Further, for a given needle model, during generating reconstruction error data table, a vertical axis of the given needle may be positioned at zero degrees from the midline, which is a vertical axis perpendicular to the detector and the compression paddle. Thus, the given needle is positioned in a vertical approach position perpendicular to the detector and the compression paddle. The tomosynthesis projection images of the respective needle in air may be obtained at various angles within the angular range of the x-ray system. The tomosynthesis projection images of needle in air may be subsequently reconstructed. An observed needle tip length and an observed needle tip end in the reconstructed volume between the detector and the compression paddle may be determined from the reconstructed images of the needle in air. The observed needle tip may be compared with an actual physical needle tip length and a needle tip end position along the z-axis to determine the reconstruction error data for the given needle model at the plurality of distances from the detector. In one example, the actual needle tip end position may be based on a target location input by the user. In this way reconstruction error data set for various needle models may be determined based on tomosynthesis reconstructed images of the various needle models in air. While the above example of determining reconstruction error data is described with respect to biopsy needle, it will be appreciated that reconstruction error data for any interventional tool may be determined as discussed above based on generating tomosynthesis projection images of corresponding interventional tool models in air.

The first data table 400 shows reconstruction error data for a needle tip end positioned at 54 mm above a top surface of the detector. The table 400 shows reconstruction error for different needle diameter (D) and needle lengths (L) combinations at 54 mm above the detector. Similarly, second data table 450 shows reconstruction error for different needle diameter (D) and needle lengths (L) combinations at 20 mm above the detector. As seen in the tables 400 and 450, the reconstruction error increases with increase in needle diameter, decrease in needle tip length, and with decreasing distance from the detector. Further, as seen in grey shaded boxes, for a given needle diameter, the reconstruction error is smallest (greater than zero) when the needle tip length is approximately two times greater than the needle diameter. Said another way, the reconstruction error is smallest (greater than zero) when the diameter is approximately half the needle tip length. Furthermore, for a given needle tip length and a given needle tip diameter, the reconstruction error increases as the needle tip end approaches closer to the detector plate.

While FIG. 4 shows two example reconstruction error data sets at two different distances from the detector, it will be appreciated that the processor may store a plurality of data sets at a plurality of distances above the detector, and also at a plurality of positions (in the x-y plane) for each of the plurality of distances above the detector (position along the z-axis) for various combinations of needle lengths and diameters.

During DBT guided biopsy, upon selecting the needle and target location and before inserting the needle into the compressed tissue, the first expected reconstruction error for the selected needle may be determined based on the error model or the reconstruction error data sets, or any combination thereof. In examples where reconstruction error data set are not available for a selected needle model, and position in the DBT volume, the error model may be used to calculate the first expected reconstruction error, and subsequently, if the determined error is greater than the threshold limit, the reconstruction data set may be used to identify one or more candidate needle models that may have smaller reconstruction error within acceptable limits as further discussed below.

In some examples, the tool expected reconstruction error may be determined for a selected interventional tool based on an error model for the selected interventional tool, the tool reconstruction error data set, or any combination thereof. Further, if the determined tool reconstruction error is greater than a threshold limit, the reconstruction error data set may be utilized to identify one or more candidate tool models that than smaller tool reconstruction error within acceptable limits.

Upon determining the expected reconstruction error Re, method 300 proceeds to 306. At 306, method 300 includes determining if the first expected reconstruction error is within a threshold error. The threshold error may be based on one or more of a size of a target (that is, size of a targeted lesion), needle tip length, needle notch position and depth, and the target location. For example, the error tolerance may be greater for larger lesions, and thus the threshold error may be greater for larger lesion. The threshold error may provide an indication as to whether the selected needle may penetrate the target tissue location and excise the target tissue when fired. In some examples, the threshold error may also be set by a user. Further, the threshold may be based on user preference. For example, the user may prefer to rely on what they see in the DBT volume and therefore use the tool that minimizes the error as much as possible. Alternatively, the user may choose to use any needle based on indication from the error model as to expected error (and the real needle tip position) in the DBT volume.

If the expected reconstruction error is not less than the threshold, the answer at 306 is NO and method 300 proceeds to 307. At 307, method 300 includes identifying one or more candidate needle models from an interventional tool database with corresponding Re less than the modelled Re (that is, first expected reconstruction error calculated at 304 based on the error model) for the given system and target parameters and less than the threshold error limit. In one example, needle models with corresponding Re may be determined based on the data table set. For example, a corresponding data table for the selected target position along the z-axis (needle tip depth along the z-axis) may be identified. Alternatively, if the data table for the selected target position is not available, a data table for a target position that closest to the selected target location may be selected. Upon identifying the data table, one or more candidate needle models with reconstruction error less than the threshold error limit may be identified from the table. Upon identifying the one or more candidate needle models, method 300 proceeds to 310.

Returning to 306, if the first expected reconstruction error is less than the threshold, the answer at 306 is YES and method 300 proceeds to 310. At 310, method 300 includes updating a reconstruction error data table for the selected target position with the first expected reconstruction error Re for the selected needle and current acquisition system. Method 300 then returns to step 212 at FIG. 2.

Returning to FIG. 2, upon determining the expected reconstruction error Re, method 200 proceeds to 214. At 214, method 200 includes before moving needle to pre-fire position, providing the first expected reconstruction error information to the user. Providing the first expected reconstructed error includes, at 216, providing an estimated position difference between the physical tip position and the reconstructed tip position. The estimated position difference may include a leaking distance along the z-axis that is expected between the actual physical tip position and the reconstructed tip position. Further, providing the first expected reconstructed error includes, at 218, providing one or more candidate needle models within the threshold error (identified at step 307) to the user. The estimated position difference and one or more candidate needle models may be provided to the user via one or more of the user interface of the x-ray system and the biopsy device user interface. In one example, the position difference may be graphically presented to the user in addition to indicating the leaking distance in a standard metric (e.g., in millimeters).

An example graphical representation of the needle tip leaking distance is shown at FIG. 5. Turning to FIG. 5, it shows a schematic illustration of an example leaking of needle tip in the z-direction in the reconstructed images due to reconstruction error. Specifically, FIG. 5 shows a portion 500 of an x-ray system, such as x-ray system 100 at FIG. 1B, between a compression paddle 502 and a detector 504. A biopsy needle 508 is included in a DBT volume 522 between the compression paddle 504 and the detector 504. The biopsy needle 508 is oriented in a vertical approach mode, wherein a vertical needle axis along a length of the needle is perpendicular to the compression paddle 502 and the detector 504. Further, the needle 508 is shown positioned slightly offset from and parallel to a vertical axis 505 (z-axis). It will be appreciated that in the vertical approach orientation, the needle 508 is oriented perpendicular to the compression paddle 502 and the detector 504, while the needle may be positioned anywhere within the DBT volume 522 and a needle tip end position may be indicated by 3D coordinates within the DBT volume, based on the target location selected by the user.

An angular range of the x-ray system is shown by arrow 506 and two angular positions $-\theta$ and $+\theta$ of an x-ray tube 520. A first cone beam of x-rays from the x-ray tube 520 at the $+\theta$ position is shown by dotted lines 540 and a second cone beam of the x-ray tube 520 at the $-\theta$ position is shown by dotted lines 545. In the present example illustration, the needle 508 is shown positioned in air within the DBT volume 522. The needle 508 may have an actual needle tip length 510 and a needle tip end 515. The needle tip portion of the needle 508 is shown by vertical hatching. However, when the needle is imaged within the DBT volume 522 by moving the x-ray tube 520 at a plurality of angles within the angular range $-\theta$ to $+\theta$, and the projection images of the x-rays projected onto the detector 504 are reconstructed, the needle tip appears in a greater DBT volume 522 along the z-axis (505) of the reconstructed images. Thus, the observed needle tip length 512 is greater than the actual needle tip length 510, and the needle tip is said to be leaking in the vertical direction along the z-axis due to reduced resolution of the DBT imaging in the z-direction. Thus, a reconstruction error, indicated by cross hatching enclosed within an area 535, of the biopsy needle may include a leaking distance of the needle tip along the z-axis. As such, an observed needle tip end 525 may be displaced from the actual needle tip end 515, and the leaking distance along the z-axis may be a position difference between the actual needle tip end position 515 and the observed needle tip end position 525. In some examples, the leaking distance may be calculated as a difference between the observed needle tip length 512 and the actual needle tip length 510.

FIG. 6 shows a schematic illustration of an example leaking of needle tip in the z-direction in the reconstructed images due to reconstruction error when a needle 608 having a smaller diameter than the needle 508 at FIG. 5 is used. As shown, the leaking distance is reduced when the needle diameter is reduced. Thus, a difference between an observed needle tip length 612 in the reconstructed images and the actual needle tip length 610 is less when a smaller diameter needle is used. Further, an actual needle tip end 615 almost coincides with the observed needle tip end 625.

In this way, depending on a type of needle, the needle tip may appear in additional image slices in the reconstructed images due to the reconstruction error. Thus the reconstruction error may include the leaking distance between the actual needle tip and the observed needle tip. By modelling the reconstruction error based on the selected needle parameters, selected target location, and the acquisition parameters, the reconstruction error may be estimated prior to inserting the needle into the compressed breast. The user may determine, based on the expected reconstruction error, that the currently selected needle may not be appropriate for biopsy, and may choose a needle (e.g., based on one or more candidate needle models with reconstruction errors less than the threshold limit presented to the user) with a smaller reconstruction error than the currently selected needle.

FIG. 7A shows a high-level method 700 for evaluating actual needle position while the needle is inserted in the compressed breast during DBT guided biopsy. Specifically, evaluating actual needle position may include inferring an actual needle tip position, and determining if the needle has bent during insertion. Further, other parameters, including reconstruction error region in the DBT image volume, and other points of interest along the needle, such as notch position, may be determined. Method 700 may be implemented by an image processing system, controller 44 at FIG. 1B, an edge device connected to the image processing system, a cloud in communication with the image processing system, or any appropriate combination thereof. Method 700 is described with regard to the systems and components of FIGS. 1B, 1C, and 1D, although it should be appreciated that method 700 may be implemented with other systems and components without departing from the scope of the present disclosure. While the method 700 and the method 800 (at FIG. 8) elaborate evaluating the actual biopsy needle position during DBT-guided biopsy, and in particular, when the needle is in the pre-fire position, it will be appreciated the methods 700 and 800 are applicable to evaluation of any position (pre-fire position, post-fire position, etc.) of any interventional tool (e.g., hook-wire, ablation needle, biopsy needle, etc.) inserted in a tissue. A high-level schematic illustrating evaluation an interventional tool position within a tissue is described at FIG. 1A.

Method 700 begins at 702. At 702, method 700 includes determining if biopsy needle selection is confirmed. The confirmation of biopsy needle selection may be based on user input. For example, the user may select a desired biopsy needle based on the first reconstruction error, and confirm the selection of the biopsy needle via a user interface, such as a user interface of the biopsy device, a user interface of the x-ray system, or a combination thereof. If the needle selection is not confirmed, the answer at 702 is NO, and method 700 proceeds to 703. At 703, method 700 includes prompting the user to confirm biopsy needle selection via the user interface. For example, the expected reconstructed error, determined based on the error model as discussed above at FIGS. 2, 3A, and 3B, for a current needle may be displayed to the user via the user interface, and an indication requesting the user to confirm if the current needle is to be used for the DBT guided biopsy procedure may be provided to the user via the user interface. Method 700 may then return to 702.

If the needle selection is confirmed, the answer at 702 is YES, and method 700 proceeds to 704. At 704, method 700 includes providing biopsy target position coordinates to a biopsy tool holder control system. The biopsy target position coordinates may be determined based on a user selecting the target position on a DBT reconstructed volume of the compressed breast prior to inserting the needle into the breast. For example, the user may select the target position for biopsy via the user interface by viewing the DBT volume represented in the first set of reconstructed images (e.g., obtained at step 208 of FIG. 2) and selecting a target portion of the breast having an abnormality (e.g., by clicking a specific point within the abnormality or an area containing the abnormality). Upon the user selecting the biopsy target position, the controller may extract the target coordinates, including an x-coordinate ($X_{target}$), a y-coordinate ($Y_{target}$), and a z-coordinate ($Z_{target}$), within the DBT volume. An example determination of target biopsy coordinates is shown at FIG. 7C.

Figure 7C:
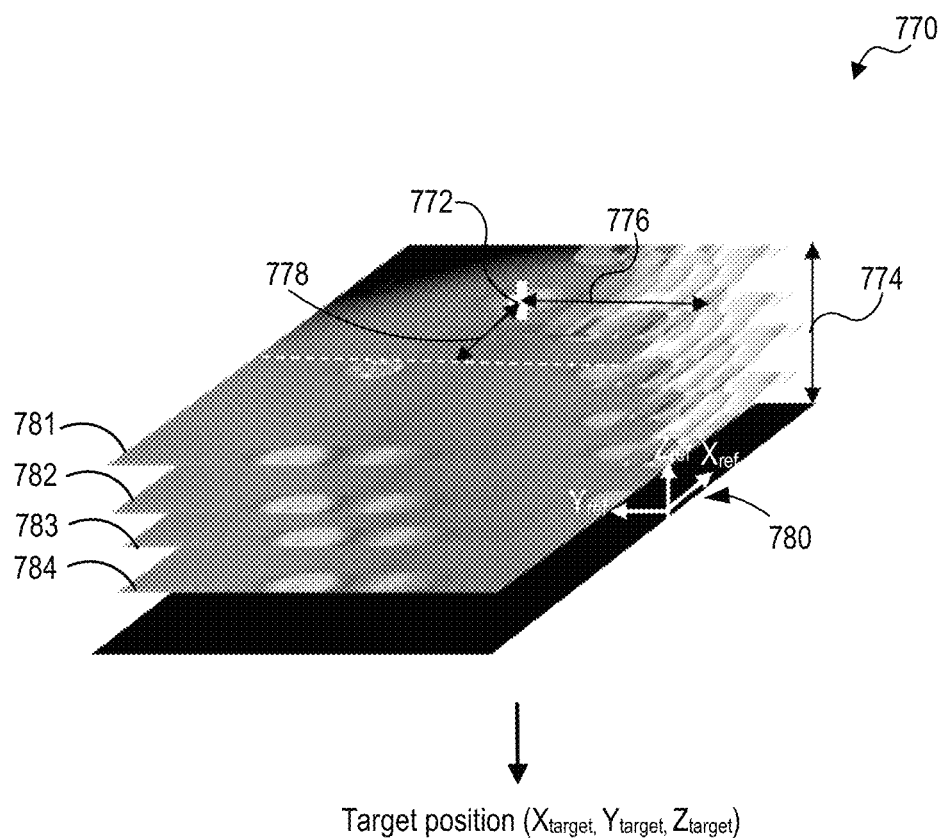
FIG. 7C shows an exemplary set of reconstructed images representing an exemplary DBT volume for target selection during a DBT guided procedure.

Turning now to FIG. 7C, a set of reconstructed images 770 representing an example DBT volume is illustrated. The set of reconstructed images 770 may be obtained by scanning the breast with the x-ray system within its angular range (−θ to +θ). The set of reconstructed images include a plurality of images 781, 782, 783, 784 reconstructed at various planes along the z-axis perpendicular to the detector. The user may view each of the plurality of images and select a plane including the target portion for biopsy. When the user makes a selection on an image, a corresponding plane is selected, and the corresponding plane provides the z-coordinate for the target position. Further, a pixel position of the target may provide the x and y coordinates respectively. Accordingly, in the present example, the user may select a target position 772 from the set of reconstructed images 770. The controller, such as the controller 44 at FIG. 1B, may determine $Z_{target}$ based on the selected plane distance 774 from a reference plane 780, $X_{target}$ and $Y_{target}$ based on X and Y coordinates 778 and 776 of a selected pixel of the target position 772 with respect to $Y_{ref}$ and $X_{ref}$ on the reference plane respectively. The reference plane may be a top surface plane of the detector, for example. Thus, based on user selection of the target position 772, target coordinates including $X_{target}$, $Y_{target}$, and $Z_{target}$ may be determined.

Upon determining the target position coordinates, the target coordinates may be communicated to the biopsy tool control system. The biopsy tool control system may command one or more actuators of a biopsy tool to position a needle guide of the biopsy gun holder at a mechanical stop position such that when the needle is inserted, a notch of the needle is in front of the lesion to puncture. That is, the needle is positioned with respect to the target coordinates ($X_{target}$, $Y_{target}$, and $Z_{target}$) determined from the reconstructed images of the DBT volume. The position where the needle is retracted into gun and as such, the needle tip is above the lesion to excise may be referred to as the pre-fire position. Upon adjusting, with the biopsy tool control system, the biopsy needle holder to a desired position such that the needle guide is at the mechanical stop position, the user may insert the biopsy needle into the compressed breast until the mechanical stop prevents further movement of the needle. That is, the biopsy needle may be inserted into the compressed breast until the needle reaches the pre-fire position, then the biopsy gun is fired and the needle reaches the post fire position. In some embodiments, the needle insertion to the pre-fire position may be automated. For example, upon an indication from the user to move the needle to pre-fire position, the biopsy holder may automatically move the biopsy needle to pre-fire position. While the present example illustrates using the biopsy tool control system to adjust the needle position, it will be appreciated that the movement of the tool including the biopsy gun and the biopsy needle may be commanded by the x-ray system controller, and is within the scope of the disclosure.

Returning to 704, as discussed above, method 700 includes sending the target position coordinates determined based on target position selection from the reconstructed images to the biopsy needle holder control system. As discussed above, the biopsy needle holder control system may then position the biopsy needle holder based on the target position coordinates and adjust the mechanical stop position on the needle guide of the biopsy gun such that when the needle is inserted into the compressed breast, either automatically by the biopsy tool control system, the x-ray system controller, or by the user, the movement of the needle is stopped (by the mechanical stop) when the needle tip is at the target position coordinates. After the needle is inserted, the biopsy tool control system may send the needle position, including the needle tip position, as determined by the biopsy tool control system to the x-ray system controller. For example, the biopsy needle holder control system may compute the needle tip position based on sensor data from a robotic system coupled to the biopsy needle holder control system, as discussed further below. The needle position returned by the biopsy tool control system (and thus, the robotic system) is the needle position in the real physical space (that is, physical volume between the compression paddle and the detector), and may be referred to as theoretical needle position.

Next, method 700 proceeds to 706. At 706, method 700 includes confirming if the needle is in pre-fire position. The pre-fire position may be confirmed based on of an input from the user indicating via the user interface that the needle is in the pre-fire position. Additionally or alternatively, the needle pre-fire position may be confirmed based on the needle position returned from the biopsy tool control system. If the needle is not in pre-fire position, the answer at 706 is NO, and the method proceeds to 707. At 707, method 700 includes monitoring user input and/or data from the biopsy needle. Method 700 may then return to determine if the needle is in pre-fire position. If the needle is at the pre-fire position, the answer at 706 is YES, and the method 700 proceeds to 708.

At 708, method 700 includes acquiring a plurality of pre-fire DBT scans with the needle in the pre-fire position. The plurality of pre-fire scans may include a scout scan acquired with the x-ray source is zero degrees from a vertical axis of the x-ray system, the vertical axis perpendicular to the top surface of the detector. The plurality of scans may further include stereo plurality of scans acquired with the x-ray source at various angles from the vertical axis (−θ to +θ) within the angular range. For example, upon confirming that the needle is at the pre-fire position, the x-ray source may be rotated within the angular range of the x-ray system and the plurality of pre-fire scans with the needle at the pre-fire position may be obtained.

Next, at 710, method 700 includes reconstructing plurality of DBT targeting images from the acquired pre-fire scans. Specifically, a plurality of projection image data sets obtained from the detector exposures during the pre-fire scanning with the x-ray tube moving within the angular range, may be reconstructed into a plurality of thin slice images (e.g., one millimeter thickness). The plurality of thin slice images from the pre-fire scan (also referred to herein as pre-fire DBT reconstructed images or simply pre-fire DBT images) may together provide a tomosynthesis reconstructed volume of the compressed breast with the needle in the pre-fire position. In some examples, additionally, two dimensional positioning images may be reconstructed from the pre-fire scan.

Continuing on to 712, the method 700 includes determining inserted needle parameters based on the pre-fire DBT images. The inserted needle parameters based on pre-fire DBT images may include a second reconstruction error of the biopsy needle in the pre-fire position, an amount of needle bending due to needle movement through the breast tissue to the pre-fire position, and an actual needle tip position. Further, the inserted needle parameters may include the target position coordinates that was determined based on DBT images acquired before the needle was adjusted to the pre-fire position, and the theoretical needle position in the real physical space determined by the biopsy tool control system (via the robotic system). Details of determining the inserted needle parameters will be described with respect to FIG. 8 below.

Figure 8:
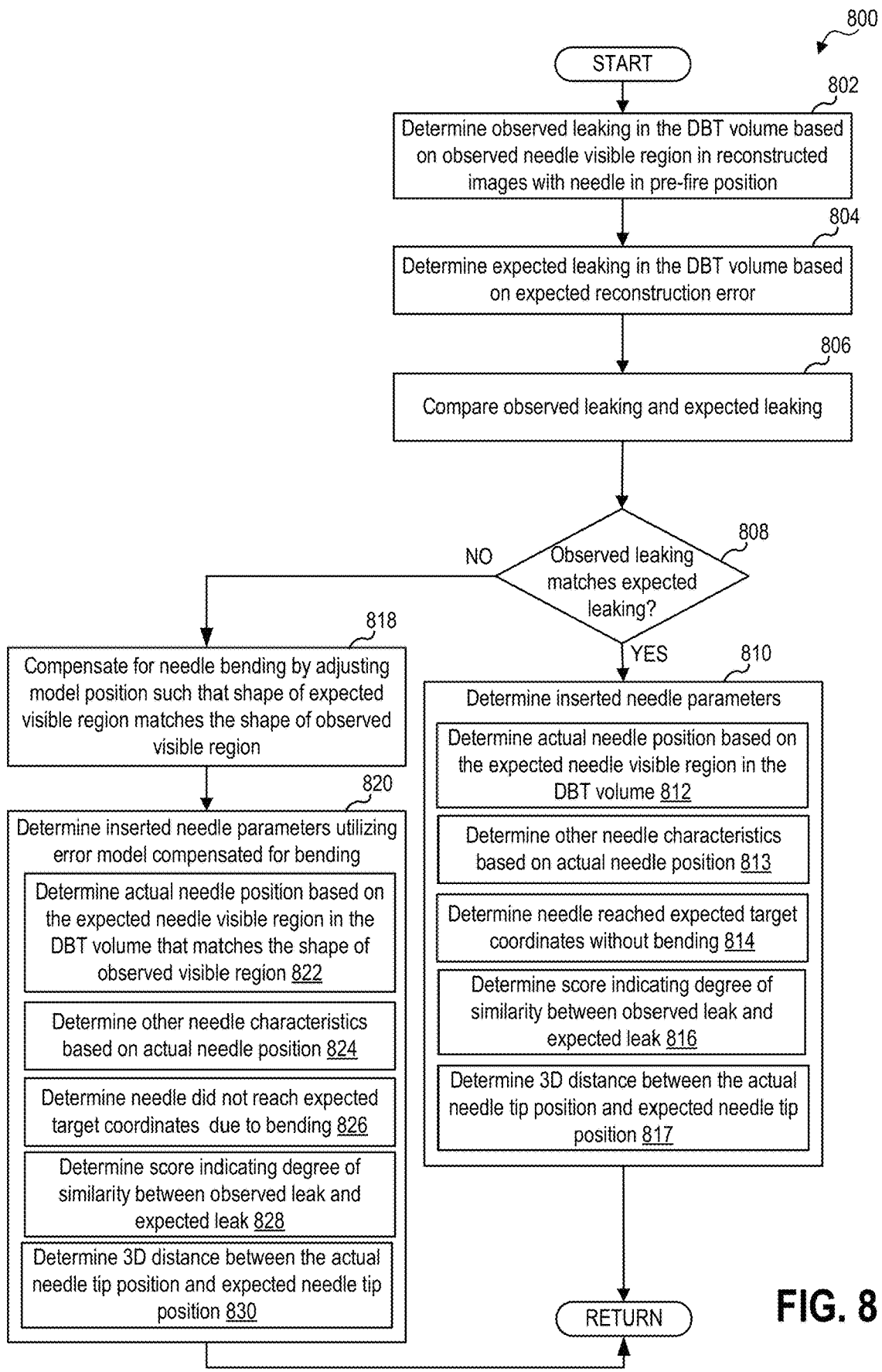
FIG. 8 is a high-level flow chart illustrating a method for determining reconstruction error of a biopsy needle and identifying needle tip location during a DBT guided biopsy procedure, according to an embodiment of the disclosure.
Figure 9:
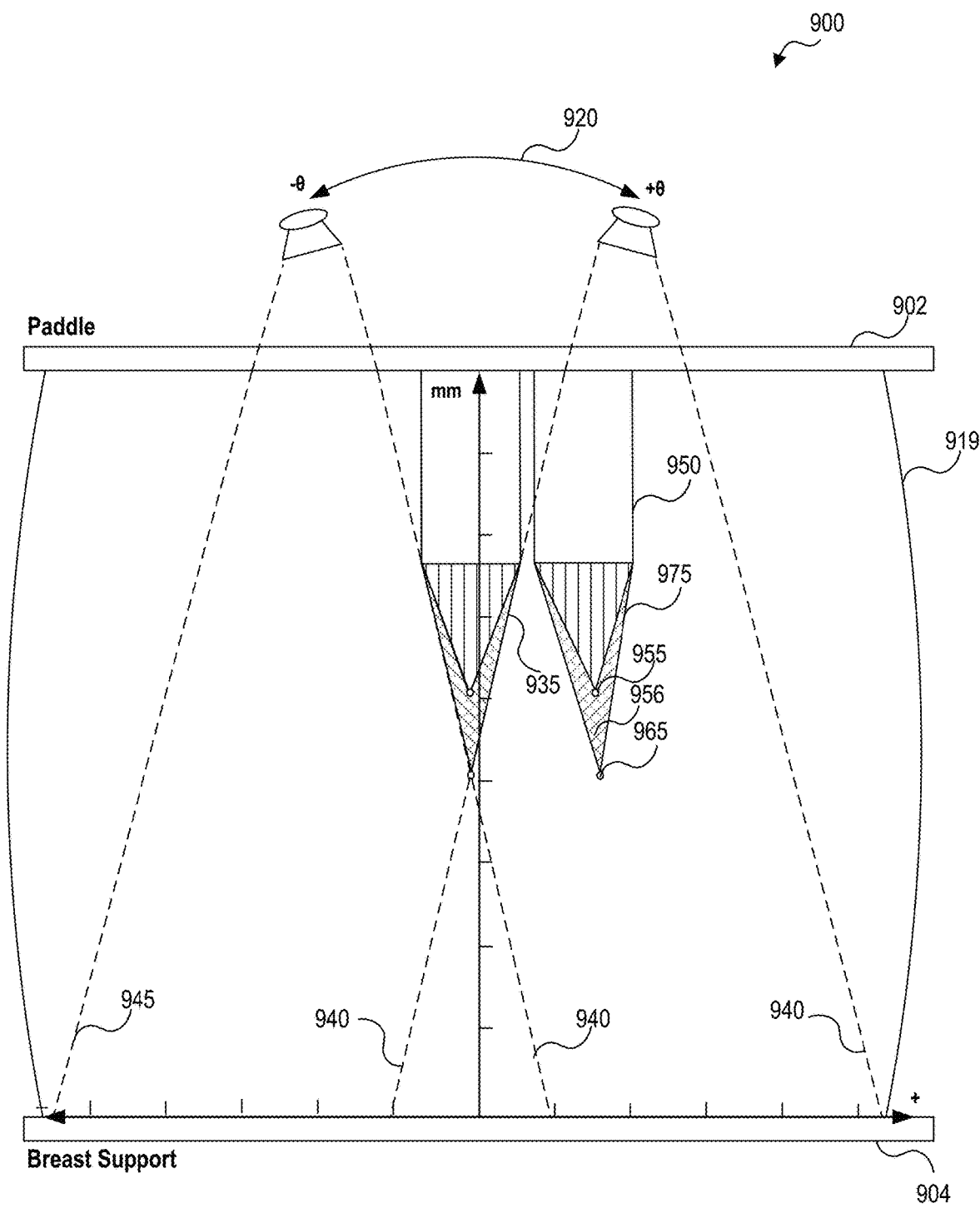
FIG. 9 is a schematic illustration of an example reconstruction error of a biopsy needle in a pre-fire position, according to an embodiment of the disclosure.

Turning to FIG. 8, a high-level flow chart 800 for determining the inserted needle parameters from the pre-fire DBT images is shown. Method 800 may be implemented by an image processing system, controller 44 at FIG. 1B, an edge device connected to the image processing system, a cloud in communication with the image processing system, or any appropriate combination thereof. Method 800 is described with regard to the systems and components of FIGS. 1B, 1C, and 1D, although it should be appreciated that method 800 may be implemented with other systems and components without departing from the scope of the present disclosure.

Method 800 begins at 802. At 802, method 800 includes determining an observed needle tip leaking volume in the DBT volume based on an observed visible volume of the needle tip in the pre-fire DBT reconstructed images. Determining the observed needle tip leaking volume may include determining the observed needle area in each of the plurality of DBT image slices, and determining the leaking volume from the observed needle area in each of the plurality of DBT image slices.

Next, method 800 proceeds to 804. At 804, method 800 includes determining an expected needle tip leaking volume based on an expected reconstruction error. The expected reconstruction error may be determined as discussed with respect to FIG. 3, and may be based on the error model. That is, the expected reconstruction error may be modelled as a function the target position coordinates, needle parameters, and acquisition system parameters. In some embodiments, the expected reconstruction error may be modelled as a function of needle position returned by the robotic system, needle parameters, and acquisition parameters. Further, the expected leaking volume may be calculated based on a minimal amount of needle bending during insertion into the breast tissue, and based on the needle tip reaching its expected target position during the insertion.

Next, upon determining the observed needle tip leaking volume and the expected needle tip leaking volume, method 800 proceeds to 806. At 806, method 800 includes comparing the observed leaking volume and the expected leaking volume. In one example, visual image processing descriptors may be utilized to compare the observed leaking and the expected leaking volume. The visual image processing descriptors may include one or more of local feature descriptors (e.g., shape, position, scale, orientation, and local image structures such as gradients, intensity, etc.,) and global feature descriptors, for example. In general, comparing the observed leaking volume and the expected leaking volume includes comparing an observed shape of the needle tip from the pre-fire DBT reconstructed images and an expected shape of the needle tip based on the error model, comparing an observed position of the needle tip from the pre-fire DBT images and an expected position of the needle tip based on the error model, and further includes comparing the observed needle tip volume and the expected needle tip leaking volume.

Next, at 808, method 800 includes determining if the observed leaking matches the expected leaking. This includes determining if the observed leaking volume is within a threshold leaking volume deviation from the expected leaking volume, if the observed position of the needle tip is within a threshold distance from the expected position of the needle tip, and further includes determining if the observed needle tip shape matches the expected needle tip shape.

If the observed leaking and the expected leaking match, method 800 proceeds to 810. At 810, method 800 includes determining inserted needle parameters. In particular, the inserted needle parameters may be determined based on the expected needle tip volume and shape modelled with the expected leaking based on the error model. That is, when the expected leaking matches the observed leaking, the actual needle is at the expected pre-fire position, and the expected leaking, including the expected needle tip volume and shape, may be utilized to determine an actual needle parameters, including the actual needle tip position. Thus, when the expected leaking matches the actual leaking, determining the inserted needle parameters may include, at 812, determining actual needle position based on the expected reconstruction error in the DBT volume. Thus, based on the expected reconstruction error of the needle tip in the pre-fire position, where the expected reconstruction error is determined based on the error model, and the observed needle leaking in the pre-fire DBT reconstructed images, the actual needle tip position (that is, the position of the needle tip in real physical volume) within the volume of the compressed breast may be determined.

Further, in an exemplary embodiment, the biopsy needle holder control system may also compute the needle tip position based on sensor data from a robotic system coupled to the biopsy needle holder control system. Specifically, in a direct model computational approach, a Cartesian tip position may be determined in real-time based on sensor feedback from the robotic system with regard to the robot axes positions, a geometric model of the robotic system, the biopsy device, the biopsy needle, and calibration parameters. That is, based on the direct model computational approach, $$(X_{tip}, Y_{tip}, Z_{tip}) = M(X_{robot}, Y_{robot}, Z_{robot}, \text{biopsy device and needle, calibration parameters})$$

Where $X_{tip}, Y_{tip}, Z_{tip}$ are cartesian coordinates of the tip position, and $M(X_{robot}, Y_{robot}, Z_{robot},$ biopsy device and needle, calibration parameters) is a direct geometrical model of the robot based on robot axes positions $X_{robot}, Y_{robot}, Z_{robot}$, biopsy device and needle dimensions, and calibration parameters.

Thus, the Cartesian tip position $(X_{tip}, Y_{tip}, Z_{tip})$ is determined based on feedback from the robotic system, and as such, may be referred to herein as robot returned tip position.

Further, the robot axes $(X_{robot}, Y_{robot}, Z_{robot})$ positions may be determined as shown below based on an inverse geometric model:

$$(X_{robot}, Y_{robot}, Z_{robot}) = M_{inv}(X_{target}, Y_{target}, Z_{target}, \text{biopsy device and needle, calibration parameters})$$

Where $X_{target}, Y_{target}, Z_{target}$ are cartesian coordinates of the target position selected from the reconstructed images, and $M_{inv}(X_{target}, Y_{target}, Z_{target},$ biopsy device and needle, calibration parameters) is an inverse geometrical model of the robot based on target position in the reconstructed image, biopsy device and needle dimensions, and calibration parameters.

In this embodiment, the robot returned tip position may be used to adjust the actual needle position information determined based on the expected reconstruction error in the DBT volume and the observed needle volume in the reconstructed images.

Further, in this embodiment, a first position of the needle tip determined based on the target tip position selected from the reconstructed images, a second position of the needle tip determined based on the tip position returned by the robot, and a third position of the needle tip determined from the pre-fire reconstructed images taking into account second reconstruction error and the observed needle volume in the pre-fire reconstructed images, may be utilized to detect one or more errors including the amount of needle bend, robot sensor errors, reconstruction algorithm errors, calibration errors, etc.

In this way, in one exemplary embodiment, the expected needle volume based on reconstruction error of the selected needle in the pre-fire position (based on error model determined as a function of needle parameters, target position parameters, and acquisition system parameters), the observed needle volume in the reconstructed image, and the robot returned tip position may be utilized to determine inserted needle parameters, including actual tip position, an amount of bend, distance between the actual tip position and expected tip position, and points of interest along the needle.

Returning to 810, in addition to determining the actual tip position at 812, determining the inserted needle parameters may include at 813, determining other needle characteristics with the respect to the target position, such as notch position in the DBT volume, based on the actual needle tip position and the known needle characteristics of the needle (e.g., diameter, length, etc.). While the above example illustrates needle characteristics, it will be appreciated that when a different interventional tool is used, the characteristics of the interventional tool may be determined. For example, tool parameters that may be taken into account may include tool portions that reach the target lesion. As an example, if a hook wire is used, a position of a hook portion of the hook wire may be determined. Further, determining the inserted needle parameters may include, at 814, indicating that the needle has reached the desired (pre-fire) position without bending (based on the expected leaking matching the observed leaking). Alternatively, if one or more of a difference volume between the observed leaking and the expected leaking is within a threshold volume, a position difference between the observed tip position and the expected tip position is within a threshold distance, and difference in shape is within a threshold limit, a degree of similarity between the observed leaking and the expected leaking may be high, and accordingly, it may be indicated that the needle has reached the pre-fire position with an amount of bending within a threshold amount.

Furthermore, at 816, a score indicating the degree of similarity between the observed leak and the expected leak may be provided. Further still, determining inserted needle parameters when the observed leaking matches (or within threshold volume deviation) from the expected leaking may include, at 817, determining the distance between the actual needle tip position and the expected needle tip position. If the observed leaking matches the expected leaking (that is, expected leaking volume and the observed leaking volume are equal, observed needle tip position and expected needle tip position are the same, and the expected leaking shape is the same as the observed leaking shape), then the actual needle tip position and the expected needle tip position coincide, and thus the distance between them is zero. Upon determining the inserted needle parameters, method 800 returns to step 716 of method 700.

Returning to 808, if the observed leaking does not match the expected leaking (either shape, position, or volume), the answer at 808 is NO, and method 800 proceeds to 818. An example illustration of needle tip in the vertical approach where the observed leaking does not match the expected leaking is shown at FIG. 9.

Continuing on to 818, method 800 includes adjusting expected reconstruction shape modelled based on the error model to match the observed needle tip shape. During some instances, when the biopsy needle is inserted into the breast, the needle trajectory may not follow an expected linear path. This may occur, for example, due to one or more of the needle tip exerting forces asymmetrically on the compressed breast, needle insertion speed, and breast deformation. For example, a beveled needle tip may follow a circular arc trajectory that may be based on needle and tissue parameters. Due to the needle bending, the observed tip shape may be different from the expected tip shape, and thus, the expected needle tip shape (which is modelled based on the needle following a linear path) may not be used to obtain the needle tip position information. Thus, when the observed needle tip leaking does not match the expected needle tip leaking, a bending function may be applied to the error model. The bending function may adjust the expected needle tip shape such that the expected needle tip shape matches the observed needle tip shape. In this way, the error model may be adjusted to compensate for needle bending. Thus, the compensated expected needle tip leaking that matches the observed leaking may now be utilized to infer the actual needle tip position. Accordingly, method 800 proceeds to 820.

At 820, method 800 includes determining pre-fire parameters using the error model that is compensated for bending. Accordingly, determining the pre-fire parameters includes, at 822, determining actual needle tip position based on the expected needle leaking compensated to match observed needle leaking. Further, in one exemplary embodiment, as discussed above with respect to 812, the robot returned actual tip position may be determined in real time, and used to calculate one or more inserted needle parameters and errors. Details of the robot returned tip position are described with respect to 812, and will not be repeated for the sake of brevity.

Further, at 824, other needle characteristics, such as notch position, with the needle in the pre-fire position in the DBT volume with respect to the target position, may be determined from the actual needle tip position, bending parameters, such as an amount of bend and needle trajectory, and known needle characteristics, such as needle diameter, needle tip length, and position of notch from the needle tip. Further, determining inserted needle parameters may include, at 826, inferring that the needle did not reach the expected target coordinates due to bending (based on the observed leaking not matching the expected leaking (as determined at 808)). Determining the inserted needle parameters may further include, at 828, determining a score indicating a degree of similarity between the observed leaking and the expected leaking. The degree of similarity may be based on one or more of a difference between the observed needle tip volume and the expected needle tip volume, a position difference between the observed needle tip position and the expected needle tip position, and a difference in shape between the observed needle tip shape and the expected needle tip shape in the reconstructed volume. Further, determining inserted needle parameters may include, at 830, determining a distance between the actual needle tip position (determined at 822) and an expected needle tip position (determined based on needle reaching the target coordinates). The distance may be calculated as distance in the three dimensional space (DBT volume).

Further, during some procedures, the targeted lesion may move when the needle is inserted even when the breast is compressed. Thus, in some embodiments, the target position may be re-selected by the user with the needle in the pre-fire position, and expected leaking in the DBT volume (step 804), and the subsequent determination of the pre-fire parameters as discussed above may be determined based on the latest selected target position.

Upon determining the inserted needle parameters, method 800 may return to step 716 at FIG. 7A.

Returning to 716, method 700 includes providing second reconstruction error information and inserted needle parameters to the user. Providing second reconstruction error information includes, at 718, indicating a reconstruction error region for the imaged needle tip in the DBT volume. The reconstruction error region may include one or more of an area between the observed needle tip shape and the expected needle tip shape, and a volume between the observed needle tip volume and the expected needle tip volume. Further, inserted needle parameters may be indicated to the users, which includes at 720, indicating the actual needle tip position; at 722, indicating the amount of bending of the needle, and indicating the distance between the actual needle tip position and the expected needle tip position; and at 724, indicating points of interest along the needle (e.g., notch position). Further, as discussed above, when a different interventional tool is used, the corresponding interventional tool parameters may be determined and displayed to the user.

In one exemplary embodiment, the second reconstruction error and inserted parameters may be displayed as an overlay on the reconstructed images, or indicated separately, or a combination of the above may be provided. The type of display may be selectable by the user. For example, the needle tip position may be indicted, via a highlight or a graphical outline, on the pre-fire DBT reconstructed images (such as pre-fire images from step 710) while other inserted needle parameters such as the amount of bend, the similarity score, the actual and expected needle tip distance, may be indicated separately. Further, based on user selection, the parameters indicated separately may be displayed as overlay on the pre-fire images. Furthermore, the reconstruction error region may be displayed as overlay on the pre-fire images based on user selection.

In another exemplary embodiment, a graphical representation of the needle tip separate from the reconstructed images may be provided.

In yet another exemplary embodiment, the second reconstruction error and one or more pre-fire parameters may be indicated via a schematic graphical illustration of each of the DBT reconstructed image slices and displayed either separately from the DBT reconstructed image slices or combined with DBT reconstructed image slices.

In this way, the second reconstruction error and the inserted needle parameters determined as discussed above, the parameters including the actual needle tip position with respect to the target position, other needle characteristics with respect to the target position, the degree of similarity, the amount of bending, and distance between the actual and expected needle tip positions, may be displayed to the user via the user interface. Further, based on the second reconstruction error and the inserted needle parameters, the user may determine whether to proceed with the current approach or if a different approach (e.g., horizontal approach) may be used for biopsy.

Upon providing the second reconstruction error and the inserted needle parameters, method 700 continues on to step 730 at FIG. 7B. At 730, method 700 includes determining if the actual needle tip position with respect to the target position is suitable for performing biopsy. This may include, in one example, determining if the user had confirmed that the selected biopsy needle is in a desired position with respect to the target position for biopsy.

Additionally or alternatively, method 700 may include indicating if the actual (current) needle tip position is in the desired position with respect to the target position based on the second reconstruction error and the inserted needle parameters. As an example, if the actual needle tip position is positioned such that the distance from the target position is greater than a threshold distance, when fired, the needle tip may not reach the target, and as such the target tissue may not be collected within the notch of the needle. The threshold distance may be based on the target position, the actual needle tip position, and needle parameters, such as length and diameter. Accordingly, the processor may indicate via the user interface that the needle tip position is not in a desired position for biopsy at the target position, and further, the processor may indicate that a distance between the actual needle tip and the target position is greater than the threshold distance. While the above step illustrates determining if the actual needle tip position with respect to the target position is suitable for performing biopsy based on user input, it will be appreciated that embodiments where the determination is automatic based on one or more of the actual tip position (from the pre-fire reconstructed images and based on reconstruction error model), target position (selected from the reconstructed images for target positioning before needle insertion), and robot returned tip position (with the tip in pre-fire position), are also within the scope of the disclosure.

If the needle tip position is not confirmed with respect to the target position, the answer at 730 is NO, and method 700 proceeds to 731, at which the current biopsy procedure with the current selected needle may be terminated. For example, based on the indications of the pre-fire parameters (at 716), the user may determine that the needle tip position is not in the desired position for biopsy. Accordingly, it may be desirable to terminate the current biopsy procedure in order to evaluate if a different approach (such as a horizontal approach if the current approach is a vertical biopsy approach), and/or a different needle may be more suitable for biopsy. Terminating the current biopsy procedure may include allowing the user to retract the needle without firing.

However, if the needle tip position is confirmed with respect to the target position for subsequent biopsy, the answer at 730 is YES, and method 700 proceeds to 734. At 734, method 700 includes transmitting confirmation of the needle tip position to the needle holder control system. In response to receiving conformation of the needle tip position, the needle holder control system, may adjust one or more actuators to allow firing of biopsy needle by the user, or to automatically initiate firing of the biopsy needle to collect biopsy samples. For example, when the needle tip position is in the desired position for biopsy with respect to the target position, the user may deploy the biopsy gun to fire the biopsy needle.

When the biopsy needle firing is complete, needle firing may be detected by one or more sensors of the biopsy device and/or the x-ray system. In response to detecting needle firing, at 735, method 700 includes obtaining a plurality of post fire images with the needle in the post fire position. The plurality of post fire images may include a scout image obtained at zero degrees with respect to the vertical axis of the x-ray system and stereo scans acquired with the x-ray source at various angles from the vertical axis (−θ to +θ) within the angular range. For example, upon confirming that the needle firing, the needle is at the post-fire position, and the x-ray source may be rotated within the angular range of the x-ray system and plurality of images with the needle at the post-fire position may be obtained. As discussed above with respect to obtaining pre-fire images, obtaining plurality of post-fire images may include obtaining plurality of post-fire scans and reconstructing plurality of post-fire images from the post-fire scans. Further, upon obtaining plurality of post-fire images, method 700 may further include displaying, on the user interface, the post-fire images with the needle in the post-fire position.

Further, as discussed above with respect to the needle in pre-fire position, needle position at the post-fire stage may be evaluated (utilizing method 800 described at FIG. 8), and the corresponding inserted needle parameters at the post-fire stage may be indicated to the user (as discussed at step 716). As the evaluation of the needle at the post-fire position is similar to the evaluation of the needle at the pre-fire position that is described in detail above, the post-fire position evaluation will not be repeated.

In one example, the evaluation of the needle at the post-fire position may be utilized to determine if the needle has penetrated the targeted lesion, and thus, evaluate the success of biopsy.

Next, at 737, method 700 may include determining if tissue extraction is complete. Determination of whether the tissue extraction is complete may be based on user confirmation, for example. If the tissue extraction is not complete, the answer at 737 is NO, and method 700 proceeds to 738 to monitor for completion of tissue extraction. When the tissue extraction is completed, the answer at 737 is YES, and method 700 proceeds to 740.

Upon extracting the tissue, the user may insert a post biopsy clip to mark the site of biopsy. Accordingly, at 740, method 700 includes determining if the post biopsy clip is inserted. For example, confirmation of post biopsy clip insertion may be based on user indication. If the post biopsy insertion is not complete, the answer at 740 is NO, and method 700 proceeds to 741 to monitor for post biopsy clip insertion. If the post biopsy clip is inserted, the answer at 740 is YES, and method 700 proceeds to 742. At 742, method 700 includes acquiring obtaining a plurality of post fire images with the post biopsy clip at the biopsy site. The plurality of post fire images with the post biopsy clip may include a scout image obtained at zero degrees with respect to the vertical axis of the x-ray system and plurality of scans acquired with the x-ray source at various angles from the vertical axis (−θ to +θ) within the angular range. For example, upon confirming that the post biopsy clip is inserted, and the x-ray source may be rotated within the angular range of the x-ray system and plurality of images with the post biopsy clip inserted may be obtained. As discussed above with respect to obtaining pre-fire images and post fire images, obtaining plurality of post-fire images with the post biopsy clip may include obtaining plurality of post-fire scans and reconstructing plurality of post-fire images from the post-fire scans. Further, method 700 includes displaying the post-fire images with the clip on the user interface.

In this way, based on first and second reconstruction errors determined based on the error model, accuracy and efficiency of biopsy may be improved.

Next, FIG. 9 shows a schematic illustration 900 of an example observed needle tip volume and shape when the biopsy needle bends during insertion to pre-fire position, and an example expected volume and shape of the needle tip without bending. Specifically, FIG. 9 shows a portion of an x-ray system, such as x-ray system 100 at FIG. 1, between a compression paddle 902 and a detector 904. A biopsy needle 950 is shown in a compressed breast volume 919. The biopsy needle 950 is oriented in a vertical approach mode, wherein a vertical needle axis along a length of the needle is perpendicular to the compression paddle 902 and the detector 904. An angular range of the x-ray system is shown by arrow 906 and two angular positions −θ and +θ of an x-ray tube 920. A first cone beam of x-rays from the x-ray tube 920 at the +θ position is shown by dotted lines 940 and a second cone beam of the x-ray tube 920 at the −θ position is shown by dotted lines 945.

In the present example illustration, the actual needle 950 is shown positioned within the DBT volume of breast 919. An expected needle shape modelled based on the error model based on needle parameters, the target position, and the x-ray system parameters is shown at 935. The needle 950 may include a needle tip end 955. The actual needle tip portion of the needle 950 is shown by vertical hatching. However, when the needle is imaged within the DBT volume by moving the x-ray tube 920 at a plurality of angles within the angular range −θ to +θ, and the projection images of the x-rays projected onto the detector 904 are reconstructed, the needle tip appears in a greater DBT volume along the z-axis (905) of the reconstructed images. Specifically, the needle tip end position 965 appears to be at a different location than the actual needle tip position 955. The observed needle tip length is greater than the actual needle tip length, and the needle tip is said to be leaking in the vertical direction along the z-axis due to reduced resolution of the DBT imaging in the z-direction. Further, during insertion, the needle tip may have followed a curved trajectory due to bending, and as a result, the observed needle tip shape 975 is different from the expected needle tip shape 935. Thus, by comparing the observed needle tip shape 975 and volume with the expected needle tip shape 935 and volume modelled based on the error model, it may be determined if the needle has followed a linear trajectory or if the needle tip has bended during the insertion. Further, an amount of bend may be determined based on the comparison of the observed needle tip shape and volume with the modelled needle tip shape and volume.

If the actual needle 950 had followed a linear path, the expected needle tip shape 935 and volume may match the observed needle tip shape and volume, and the modeled needle tip may be used to determine the actual needle tip end. However, since the actual needle tip 950 followed a curved trajectory, in order to determine the actual needle tip position 955, the expected needle tip 935 modelled based on the error model, may be adjusted such that the expected needle tip shape 935 and volume matches the observed needle tip shape 975 and volume. Upon adjusting the expected needle tip shape and volume to the observed needle tip shape and volume, the actual needle tip end position 955 may be inferred from the adjusted model. Further, a leaking volume 956 may be determined from the adjusted needle tip model and the observed needle tip.

In this way the error model and the observed needle volume may be utilized to infer if the actual needle was bent during insertion, and further determine an actual needle tip position. The actual needle tip position, the leaking volume of the actual needle tip volume, the amount of bending of the actual needle tip, and other needle parameters, such as notch position, may be indicated to the user, Based on the above indications, the user may be able to visualize the actual needle tip position more accurately, and determine is the needle is at the desired position with respect to the target position for biopsy.

A technical effect is that the error model allows the user to determine the actual interventional tool position with greater accuracy. By implementing the error model, the user is able to perform the interventional procedure with increased accuracy and efficiency, and further, the error model facilitates the user in more accurate decision making process at various stages of workflow. As a result, the need to re-do the interventional procedure, for example, due to not extracting the targeted abnormality is significantly reduced. Another technical effect of the error model is that user may be informed of the expected reconstruction error even before beginning the interventional procedure, and may be able to decide whether the expected reconstruction error is acceptable for a given interventional procedure, thereby increasing efficiency and improving success rate of the interventional procedure.

An embodiment for a method for an x-ray system comprises performing a digital breast tomosynthesis scan on a compressed breast with the x-ray system and generating tomosynthesis scan data; reconstructing images of the compressed breast from the tomosynthesis scan data; and determining an expected reconstruction error for an interventional tool based on an error model modelled as a function of acquisition geometry of the x-ray system and interventional tool parameters; wherein the interventional tool parameters include a tool length, a tool tip diameter, a tool orientation, and a tool tip position, the tool tip position derived from one or more of a selected target position in the reconstructed images and a robot returned tip position determined based on feedback from a robotic system coupled to the x-ray system. A first example of the method includes wherein the expected reconstruction error for the interventional tool is determined before the interventional tool is inserted into compressed breast. In a second example of the method, which optionally includes the first example, the interventional tool includes one or more of a biopsy needle, a hook wire, and an ablation needle; and wherein the acquisition geometry includes an angular range of the x-ray system, a source-to-image distance for the x-ray system, and a focal spot position for the x-ray system. In a third example of the method, which optionally includes one or both of the first and second examples, the method further includes displaying the expected reconstruction error on a user interface of the x-ray system. In a fourth example of the method, which optionally includes one or more or each of the first through third examples, the method further includes identifying one or more candidate interventional tools from an interventional tool database having a respective reconstruction error less than a threshold error; and displaying the one or more candidate interventional tools on the user interface. In a fifth example of the method, which optionally includes one or more or each of the first through fourth examples, the method further includes wherein the threshold error is based on one or more of a size of a selected target, the interventional tool parameters and user selected setting. In a sixth example of the method, which optionally includes one or more or each of the first through fifth examples, the method includes responsive to the interventional tool positioned within the compressed breast, performing a second tomosynthesis scan of the compressed breast with the interventional tool and reconstructing second images based on second scan data from the second tomosynthesis scan; determining an actual tool tip end position based on an observed tool tip shape and position from the second reconstructed images, and the expected reconstruction error; and indicating the actual tool tip position on the second reconstructed images. In a seventh example of the method, which optionally includes one or more or each of the first through sixth examples, the method further includes determining an amount of tool tip shift based on a comparison of the observed tool tip shape and position in the second reconstructed images with an expected tool tip shape and position, the expected tool tip shape and position modelled based on the expected reconstruction error and the tool tip position. In an eighth example of the method, which optionally includes one or more or each of the first through seventh examples, the method further includes wherein the comparison is performed using a similarity metric; and further comprising indicating the amount of tool tip shift on the user interface.

An embodiment is directed to a method for an image guided interventional procedure with an x-ray system, the method comprises: when an interventional tool is inserted in a tissue, performing a tomosynthesis scan of the tissue with the interventional tool in the tissue and reconstructing images based on scan data from the second tomosynthesis scan; determining an expected reconstruction error for the interventional tool, the expected reconstruction error based on a target position, x-ray system geometry, and one or more interventional tool parameters; determining an observed tool tip shape from the reconstructed images; determining an expected tool tip shape from the tool tip position and the expected reconstruction error; determining a similarity metric between the observed tool tip shape and the expected tool tip shape; and determining an actual tool tip end position within a physical volume of the tissue based on the similarity metric. A first example of the method includes wherein when inserted, the tool is in a pre-fire position with respect to the target position. In a second example of the method, which optionally includes the first example, and further includes wherein when inserted, the tool is in a post-fire position with respect to the target position. In a third example of the method, which optionally includes one or both of the first and second examples, the method further includes wherein the expected reconstruction error includes an estimated tool tip position difference between an actual tool tip position and an expected reconstructed tip position, the actual tool tip position based on the target position, and the expected reconstruction tip position based on the target position, the x-ray system geometry, and the one or more interventional tool parameters; and wherein the one or more interventional tool parameters include a desired orientation of the tool, a length of the tool tip, and a diameter of the tool tip. In a fourth example of the method, which optionally includes one or more or each of the first through third examples, the method further includes displaying the reconstructed images on the user interface; indicating one or more of the expected tool tip position, the actual tool tip position and a leaking area of the selected interventional tool on the reconstructed images containing the tool, and displaying the expected reconstruction error on the user interface; wherein the leaking area is based on the expected reconstruction error. In a fifth example of the method, which optionally includes one or more or each of the first through fourth examples, the method further includes determining an amount of tool shift based on the similarity metric, and displaying the amount of tool shift on the user interface. In a sixth example of the method, which optionally includes one or more or each of the first through fifth examples, the method includes determining a sensor based tool tip position of the tool when the tool is inserted in the tissue; and adjusting the determined the actual tool tip position information based on the sensor based tool tip position; wherein the sensor based tool tip position is determined as a function of axis positions of a robotic tool used for mounting and guiding the interventional, a geometric model of the robotic tool, the interventional tool parameters, and calibration parameters of the interventional tool.

An embodiment for a system for an imaging system comprises: a radiation source rotating within an angular range about an axis of the imaging system; a detector for receiving radiation rays from the radiation source and generating a plurality of projection images of a specimen positioned between the radiation source and the detector; a biopsy device including a biopsy tool system and an interventional tool coupled to the biopsy tool system, the biopsy device coupled to the imaging system and positioned between the radiation source and the detector; and an imaging processor with executable instructions stored in non-transitory memory for: reconstructing a plurality of projection images of the specimen without the tool inserted from a first digital breast tomosynthesis scan; determining an expected reconstruction error for the tool based on a selected target biopsy position in the reconstructed images, the x-ray system geometry, and tool parameters including a tool diameter and a tool length; and displaying the expected reconstruction error on a user interface of the imaging system. In a first example of the system, the imaging system further includes wherein the expected reconstruction error includes an expected leaking of a tool tip image within an imaging volume of the x-ray system. In a second example of the imaging system, which optionally includes the first example, the processor includes further instructions in non-transitory memory for: generating second set of images by reconstructing a plurality of second projection images of the specimen with the tool inserted, the plurality of second projection images obtained from a second digital breast tomosynthesis scan with the imaging system; determining an observed tool tip image from the second images; determining one or more of an actual tool tip position, an actual tool tip shape, a reconstruction error region, and an amount of bend of the tool, based on an expected position and expected shape of the tool tip modelled from the expected reconstruction error, and based on the observed position and observed shape of the observed tool tip image; and indicating the actual tool tip position and the reconstruction error region on the second images displayed on the user interface; and displaying the amount of bend on the user interface. In a third example of the imaging system, which optionally includes the first and the second examples, the imaging system includes wherein the tool is a needle; and wherein the processor includes further instructions for: determining an actual notch position of the needle based on an observed needle tip shape and an observed needle tip position from tomosynthesis reconstructed images of the needle, and a corresponding expected reconstruction error for the needle.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an x-ray system, comprising:
performing a digital breast tomosynthesis scan on a compressed breast with the x-ray system and generating tomosynthesis scan data;
reconstructing images of the compressed breast from the tomosynthesis scan data; and
determining an expected reconstruction error for an interventional tool based on an error model modelled as a function of acquisition geometry of the x-ray system and interventional tool parameters;
wherein the interventional tool parameters include a tool length, a tool tip diameter, a tool orientation, and a tool tip position, the tool tip position derived from one or more of a selected target position in the reconstructed images and a robot returned tip position determined based on feedback from a robotic system coupled to the x-ray system.

2. The method of claim 1, wherein the expected reconstruction error for the interventional tool is determined before the interventional tool is inserted into compressed breast.

3. The method of claim 1, wherein the interventional tool includes one or more of a biopsy needle, a hook wire, and an ablation needle; and wherein the acquisition geometry includes an angular range of the x-ray system, a source-to-image distance for the x-ray system, and a focal spot position for the x-ray system.

4. The method of claim 1, further comprising displaying the expected reconstruction error on a user interface of the x-ray system.

5. The method of claim 1, further comprising, identifying one or more candidate interventional tools from an interventional tool database having a respective reconstruction error less than a threshold error; and displaying the one or more candidate interventional tools on the user interface.

6. The method of claim 5, wherein the threshold error is based on one or more of a size of a selected target, the interventional tool parameters and user selected setting.

7. The method of claim 1, further comprising:
responsive to the interventional tool positioned within the compressed breast, performing a second tomosynthesis scan of the compressed breast with the interventional tool and reconstructing second images based on second scan data from the second tomosynthesis scan;
determining an actual tool tip end position based on an observed tool tip shape and position from the second reconstructed images, and the expected reconstruction error; and
indicating the actual tool tip position on the second reconstructed images.

8. The method of claim 7, further comprising determining an amount of tool tip shift based on a comparison of the observed tool tip shape and position in the second reconstructed images with an expected tool tip shape and position, the expected tool tip shape and position modelled based on the expected reconstruction error and the tool tip position.

9. The method of claim 8, wherein the comparison is performed using a similarity metric; and further comprising indicating the amount of tool tip shift on the user interface.

10. A method for an image guided interventional procedure with an x-ray system, comprising:
when an interventional tool is inserted in a tissue, performing a tomosynthesis scan of the tissue with the interventional tool in the tissue and reconstructing images based on scan data from a the second tomosynthesis scan;
determining an expected reconstruction error for the interventional tool, the expected reconstruction error based on a target position, x-ray system geometry, and one or more interventional tool parameters;
determining an observed tool tip shape from the reconstructed images;
determining an expected tool tip shape from the tool tip position and the expected reconstruction error;
determining a similarity metric between the observed tool tip shape and the expected tool tip shape; and
determining an actual tool tip end position within a physical volume of the tissue based on the similarity metric.

11. The method of claim 10, wherein when inserted, the tool is in a pre-fire position with respect to the target position.

12. The method of claim 10, wherein when inserted, the tool is in a post-fire position with respect to the target position.

13. The method of claim 10, wherein the expected reconstruction error includes an estimated tool tip position difference between an actual tool tip position and an expected reconstructed tip position, the actual tool tip position based on the target position, and the expected reconstruction tip position based on the target position, the x-ray system geometry, and the one or more interventional tool parameters; and wherein the one or more interventional tool parameters include a desired orientation of the tool, a length of the tool tip, and a diameter of the tool tip.

14. The method of claim 13, further comprising displaying the reconstructed images on the user interface; indicating one or more of the expected tool tip position, the actual tool tip position and a leaking area of the selected interventional tool on the reconstructed images containing the tool, and displaying the expected reconstruction error on the user interface; wherein the leaking area is based on the expected reconstruction error.

15. The method of claim 10, further comprising determining an amount of tool shift based on the similarity metric, and displaying the amount of tool shift on the user interface.

16. The method of claim 10, further comprising determining a sensor based tool tip position of the tool when the tool is inserted in the tissue; and adjusting the determined the actual tool tip position information based on the sensor based tool tip position; wherein the sensor based tool tip position is determined as a function of axis positions of a robotic tool used for mounting and guiding the interventional, a geometric model of the robotic tool, the interventional tool parameters, and calibration parameters of the interventional tool.

17. An imaging system, comprising:
a radiation source rotating within an angular range about an axis of the imaging system;
a detector for receiving radiation rays from the radiation source and generating a plurality of projection images of a specimen positioned between the radiation source and the detector;
a biopsy device including a biopsy tool system and an interventional tool coupled to the biopsy tool system, the biopsy device coupled to the imaging system and positioned between the radiation source and the detector; and
an imaging processor with executable instructions stored in non-transitory memory for:
reconstructing a plurality of projection images of the specimen without the tool inserted from a first digital breast tomosynthesis scan;
determining an expected reconstruction error for the tool based on a selected target biopsy position in the reconstructed images, the x-ray system geometry, and tool parameters including a tool diameter and a tool length; and
displaying the expected reconstruction error on a user interface of the imaging system.

18. The system of claim 17, wherein the expected reconstruction error includes an expected leaking of a tool tip image within an imaging volume of the x-ray system.

19. The system of claim 18, wherein the processor includes further instructions in non-transitory memory for:
generating second set of images by reconstructing a plurality of second projection images of the specimen with the tool inserted, the plurality of second projection images obtained from a second digital breast tomosynthesis scan with the imaging system;
determining an observed tool tip image from the second images;
determining one or more of an actual tool tip position, an actual tool tip shape, a reconstruction error region, and an amount of bend of the tool, based on an expected position and expected shape of the tool tip modelled from the expected reconstruction error, and based on the observed position and observed shape of the observed tool tip image; and
indicating the actual tool tip position and the reconstruction error region on the second images displayed on the user interface; and displaying the amount of bend on the user interface.

20. The system of claim 19, wherein the tool is a needle; and wherein the processor includes further instructions for: determining an actual notch position of the needle based on an observed needle tip shape and an observed needle tip position from tomosynthesis reconstructed images of the needle, and a corresponding expected reconstruction error for the needle.

* * * * *